United States Patent [19]

Pfeifer et al.

[11] Patent Number: 4,698,295

[45] Date of Patent: Oct. 6, 1987

[54] POLYIMIDES, A PROCESS FOR THEIR PREPARATION AND THEIR USE, AND TETRACARBOXYLIC ACIDS AND TETRACARBOXYLIC ACID DERIVATIVES

[75] Inventors: Josef Pfeifer, Therwil; Rudolf Duthaler, Zurich, both of Switzerland

[73] Assignee: Ciba-Geigy Corporation, Ardsley, N.Y.

[21] Appl. No.: 796,380

[22] Filed: Nov. 8, 1985

[30] Foreign Application Priority Data

Nov. 16, 1984 [CH] Switzerland .................. 5486/84

[51] Int. Cl.$^4$ .................. G03C 5/00; B03D 3/06
[52] U.S. Cl. .................. 430/325; 430/270; 427/54.1; 522/904; 522/905; 522/148; 522/164
[58] Field of Search ............... 430/270, 325; 427/54.1; 522/904, 905, 148, 164

[56] References Cited

U.S. PATENT DOCUMENTS

| | | | |
|---|---|---|---|
| 3,275,690 | 9/1966 | Stroh et al. ................ | 260/576 |
| 3,591,661 | 7/1971 | Rodgers ................ | 522/904 X |
| 3,702,318 | 11/1972 | Browning ................ | 260/47 CP |
| 3,787,367 | 1/1974 | Farrissey et al. ................ | 260/65 |
| 3,926,641 | 12/1975 | Rosen ................ | 522/905 X |
| 4,030,948 | 6/1977 | Berger ................ | 148/33.3 |
| 4,146,723 | 3/1979 | Findeisen et al. ................ | 548/307 |
| 4,331,705 | 5/1982 | Samudrala ................ | 427/54.1 |
| 4,349,619 | 9/1982 | Kamoshida et al. ................ | 430/196 |
| 4,395,527 | 7/1983 | Berger ................ | 528/26 |
| 4,480,009 | 10/1984 | Berger ................ | 428/447 |
| 4,499,149 | 2/1985 | Berger ................ | 428/447 |
| 4,578,166 | 3/1986 | Uno et al. ................ | 522/164 X |

FOREIGN PATENT DOCUMENTS 1962588 7/1970 Fed. Rep. of Germany .

OTHER PUBLICATIONS

CA, 98, 215300g (1983).
Z. Jedlinski et al, Makromol Chem. 183, 1615 (1982).

*Primary Examiner*—John E. Kittle
*Assistant Examiner*—Cynthia Hamilton
*Attorney, Agent, or Firm*—Luther A. R. Hall

[57] ABSTRACT

Polyimides which essentially consist of 0.1 to 100 mol % of at least one structural element of the formula I

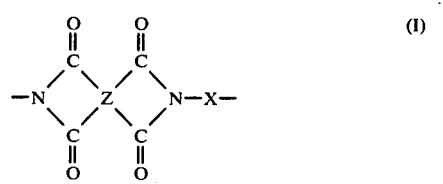

and 99.9 to 0 mol % of at least one structural element of the fomula II and/or III

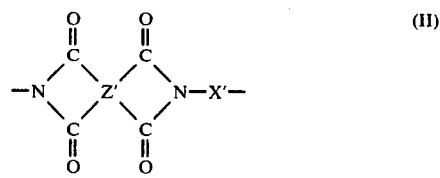

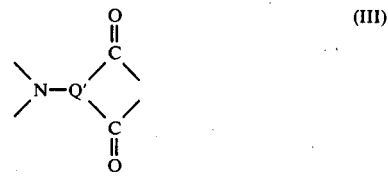

in which and Z' are a tetravalent aromatic radical, Q' is a trivalent aromatic radical, X and X' are a divalent radical of an organic amine are autophotocrosslinkable. They are suitable for the production of protective films and photographic relief images.

38 Claims, No Drawings

POLYIMIDES, A PROCESS FOR THEIR PREPARATION AND THEIR USE, AND TETRACARBOXYLIC ACIDS AND TETRACARBOXYLIC ACID DERIVATIVES

The present invention relates to homo- and copolyimides of aromatic tetracarboxylic acids containing a carbonyl group and diamines and, if appropriate, aromatic aminodicarboxylic acids, a process for their preparation and their use for the preparation of protective films or photographic relief images. The present invention furthermore relates to novel tetracarboxylic acids and acid derivatives thereof.

Polyimides are plastics with useful thermomechanical properties. However, because of their high melting ranges, they cannot be processed by the shaping methods customary for thermoplastics. Soluble polyimides which can be used as varnishes to form protective coatings of high heat stability have therefore been developed, c.f. German Auslegeschrift 1,962,588 and U.S. Pat. No. 3,787,367. With the development of electronics and semiconductor technology, high requirements are imposed on the heat stability of polyimides, for example as insulating and protective films. There is also the desire for polyimides which are photocrosslinkable and can be used in electronics and semiconductor technology, for example as a resist material.

It has now been found that soluble and autophotocrosslinkable polyimides are obtained if tetracarboxylic acids in which aromatic radicals are linked via a carbonyl group are used.

The invention relates to homo- and copolyimides of at least one aromatic tetracarboxylic acid and at least one diamine, which essentially contain 0.1 to 100 mol % of at least one structural element of the formula I

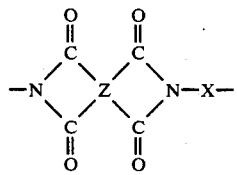

(1)

and 99.9 to 0 mol % of at least one structural element of the formulae II and/or III

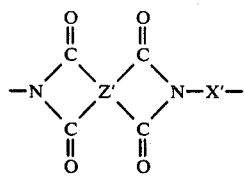

(II)

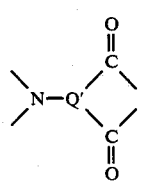

(III)

in which Z is at least one tetravalent radical of the formula IV, V, VI or VII

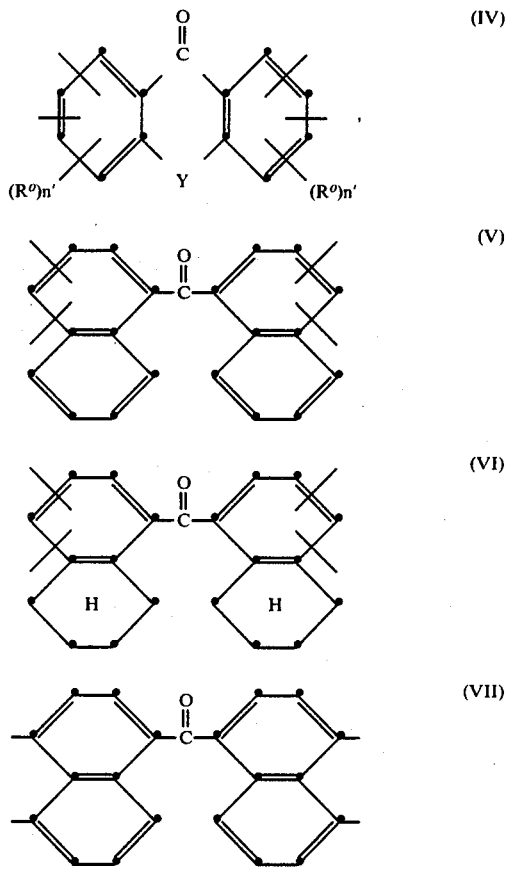

in which the free bonds are in the ortho-position relative to one another and Y is a direct bond, —CH$_2$—, —(CH$_2$)$_2$—, —O—, —S—, —SO—, —SO$_2$—, —CO—, —NR— or —CRR$^1$—, in which R is a hydrogen atom, C$_1$–C$_{10}$-alkyl, phenyl, naphthyl or phenyl-(C$_a$H$_{2a}$)—, where a is 1 to 4, and R$^1$ is R, with the exception of a hydrogen atom, R$^0$ is C$_1$–C$_{10}$-alkyl, halogen, —CN, —NO$_2$, C$_1$–C$_{12}$-alkoxy, phenoxy, naphthoxy or phenyl(C$_a$H$_{2a}$)—, where a is 1–4, n' is 0, 1 or 2, X is an unsubstituted or substituted divalent aliphatic radical, which can be interrupted by heteroatoms or aromatic, heterocyclic or cycloaliphatic groups, a substituted or unsubstituted heterocyclic, cycloaliphatic or araliphatic radical, an aromatic radical, in which two aryl nuclei are linked via an aliphatic group, or an aromatic radical which is substituted by at least one alkyl group, cycloalkyl group, alkoxy group, alkoxyalkyl group, alkylthio group, alkylthioalkyl group, hydroxyalkyl group, hydroxyalkoxy group, hydroxyalkylthio group, aralkyl group or, in the case of two adjacent C atoms of the aromatic radical, by an alkylene group, Q' is a trivalent aromatic radical, Z' has the same meaning as Z or is a tetravalent organic radical other than Z and X' is the divalent radical, other than X, of an organic diamine, and in which Z in formula I can also be a tetravalent benzophenone radical if structural elements of the formula III are present.

The structural elements of the formula I are preferably present in an amount of 5–100 mol %, preferably 30–100 mol %, in particular 60–100 mol % and especially 80–100 mol %, and the structural elements of the formula II and/or III are preferably present in an amount of 95 –0 mol %, preferably 70 –0 mol %, in particular 60 to 0 mol % and especially 20 to 0 mol %.

The free bonds in the radicals of the formulae IV to VI are preferably in the meta- or para-position relative to the CO group.

Alkyl or alkoxy $R^0$ can be linear or branched, and preferably contains 1 to 4 C atoms. Examples are methyl, methoxy, ethyl, ethoxy, n-propyl, n-propoxy, isopropyl, isopropoxy, butyl and butoxy. Halogen $R^0$ is preferably chlorine, and in the —$C_aH_{2a}$— group, a is preferably 1 or 2. n' in formula IV is preferably 0.

Alkyl R or $R^1$ preferably contains 1 to 4 C atoms. The alkyl can be linear or branched. Examples are methyl, ethyl, n-propyl, isopropyl and butyl. In the —($C_aH_{2a}$)— group, a is preferably 1 or 2.

Y in formula IV is preferably a direct bond, —O—, —S—, —$CH_2$— or —CO—.

A radical Z' other than Z preferably contains, as a tetravalent aromatic radical, 6 to 30, in particular 6 to 20, C atoms. In a preferred sub-group, Z' has the formula

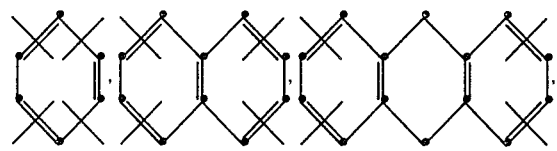

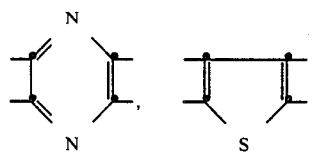

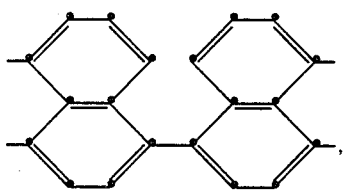

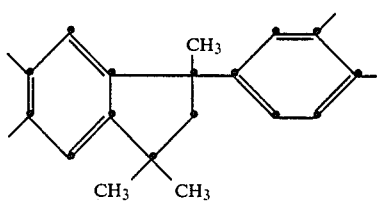

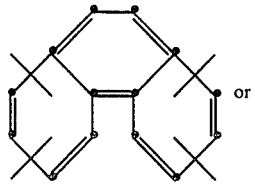

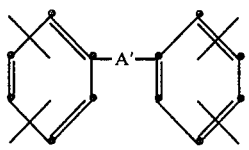

in which A' is a direct bond or a bridge group of the formula

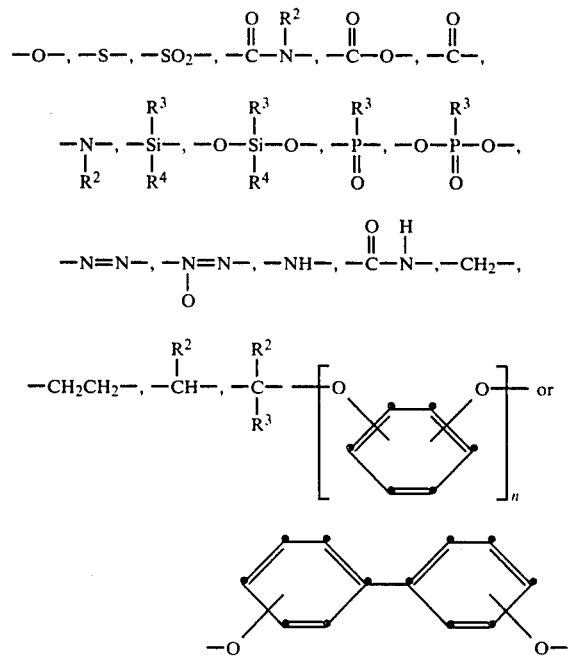

in which $R^2$, $R^3$ and $R^4$ are alkyl with 1 to 6 C atoms, phenyl or benzyl, $R^3$ and $R^4$ are alkoxy with 1 to 6 C atoms, phenoxy or benzyloxy and n is 0, 1, 2 or 3.

In the above formulae, two of the free bonds are in each case always in the peri- and/or ortho-position.

A preferred sub-group for Z' are radicals of the formulae

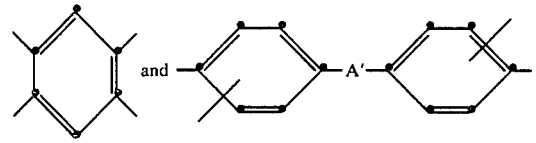

in which A' is a direct bond, —O—, —$SO_2$—, —$CH_2$— or, in particular, —CO—.

Especially preferred radicals are those of the formulae

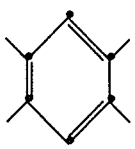

and, in particular

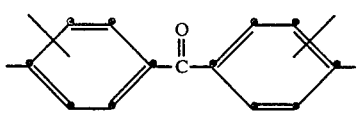

or mixtures thereof, for example those with at least 5 mol % of tetravalent benzophenone radicals. The free bonds in the benzophenone radical are in the ortho-position. It has been found that benzophenone radicals likewise lead to autophotocrosslinkable polyimides. In the case of smaller contents of structural elements of the formula I, the photosensitivity can be increased by a content of benzophenonetetracarboxylic acid imide units.

Examples of tetracarboxylic acid anhydrides with a radical Z′ are: 2,3,9,10-perylenetetracarboxylic acid dianhydride, 1,4,5,8-naphthalenetetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, pyromellitic acid dianhydride, 3,3′,4,4′-biphenyltetracarboxylic acid dianhydride, 2,2′,3,3′-biphenyltetracarboxylic acid dianhydride, 4,4′-isopropylidenediphthalic acid anhydride, 3,3′-isopropylidenediphthalic acid anhydride, 4,4′-oxydiphthalic acid anhydride, 4,4′-sulfonyldiphthalic acid anhydride, 3,3′-oxydiphthalic acid anhydride, 4,4′-methylenediphthalic acid anhydride, 4,4′-thiodiphthalic acid anhydride, 4,4′-ethylidenediphthalic acid anhydride, 2,3,6,7-naphthalenetetracarboxylic acid dianhydride, 1,2,4,5-naphthalenetetracarboxylic acid dianhydride, 1,2,5,6-naphthalenetetracarboxylic acid dianhydride, benzene-1,2,3,4-tetracarboxylic acid dianhydride, thiophene2,3,4,5-tetracarboxylic acid dianhydride, 1-(3′,4′-dicarboxyphenyl)-1,3,3-trimethylindane-5,6-dicarboxylic acid dianhydride, 1-(3′,4′-dicarboxyphenyl)-1,3,3-trimethylindane-6,7-dicarboxylic acid dianhydride, 1-(3′,4′-dicarboxyphenyl)-3-methylindane-5,6-dicarboxylic acid dianhydride, 1-(3′,4′-dicarboxyphenyl)-3-methylindane-6,7-dicarboxylic acid dianhydride, 3,3′,4,4′-benzophenonetetracarboxylic acid anhydride and 4,5,3′,4′-benzophenonetetracarboxylic acid anhydride.

Q′ in formula III is the trivalent aromatic radical of an aminodicarboxylic acid. The aromatic radicals are preferably mononuclear or dinuclear phenyl radicals, such as, for example, phenyl, naphthyl or bisphenylenes. The radicals can be substituted by halogen, for example chlorine, or cyano or nitro. In a preferred embodiment, Q′ in formula III is a trivalent radical of the formula

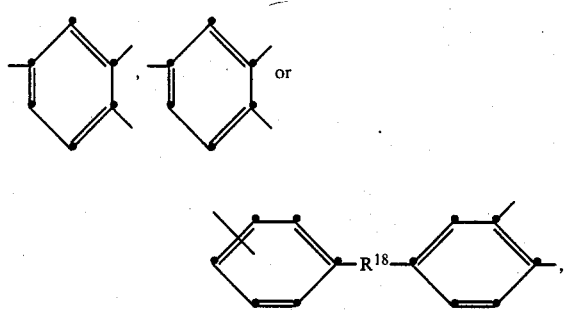

in which the free bond is in the meta- or para-position relative to the $R^{18}$ group and $R^{18}$ is a direct bond or a bridge group. Suitable bridge groups are, for example, $-CH_2-$, $-O-$, $-S-$ and, in particular, $-CO-$. The trivalent radical particularly preferably has the formula

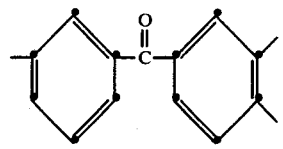

If the polyimides contain a radical of the formula III, Z in formula I can also be only the tetravalent radical of a benzophenonetetracarboxylic acid, for example of the formula

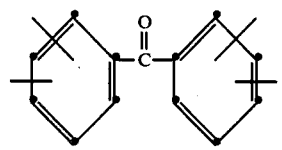

in which the free bonds are in the ortho-position.

X in the structural element of the formula I contains, as a divalent aliphatic radical, preferably 2 to 30 C atoms, as a heterocyclic radical, preferably 3 to 5 ring C atoms and 1 or 2 heteroatoms, for example N, O or S, as a cycloaliphatic radical, 5 to 8 ring C atoms, as an araliphatic radical, 7 to 30 C atoms, as an aromatic radical with linked aryl nuclei, 13 to 30 C atoms, and as a substituted aromatic radical, 7 to 30 C atoms. X is more preferably an aliphatic radical with 3 to 30 C atoms, a cycloaliphatic radical with 5–8 ring C atoms, an araliphatic radical with 7 to 30 C atoms or a substituted aromatic radical with 7 to 30 C atoms.

A divalent aliphatic radical X in formula I preferably contains 6 to 30, and in particular 6 to 20 C atoms. In a preferred sub-group, X is linear or branched alkylene, which can be interrupted by oxygen atoms, $-NH-$, $-NR^a-$, $-\oplus NR_2{}^a G^{63}-$, cyclohexylene, naphthylene, phenylene or hydantoin radicals. $R^a$ can be, for example, alkyl with 1 to 12 C atoms or cycloalkyl with 5 or 6 ring C atoms, phenyl or benzyl. $G^{63}$ is an anion of a proton acid, for example a halide, sulfate or phosphate. In a preferred embodiment, X is linear or branched alkylene with 6 to 30 C atoms, $-(CH_2)_m-R^{13}-(CH_2)_n-$, in which $R^{13}$ is phenylene, naphthylene, cyclopentylene or cyclohexylene and m and n independently of one another are the number 1, 2 or 3, $-R^{14}-(OR^{15})_p-O-R^{14}-$, in which $R^{14}$ is ethylene, 1,2-propylene, 1,3-propylene or 2-methyl-1,3-propylene and $R^{15}$ is ethylene, 1,2-propylene, 1,2-butylene, 1,3-propylene or 1,4-butylene, and p is a number from 1 to 100, or

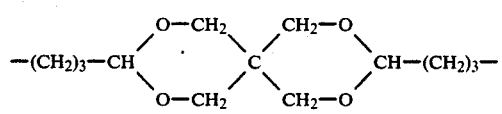

Examples of aliphatic radicals are: methylene, ethylene, 1,2- or 1,3-propylene, 2,2-dimethyl-1,3-propylene, 1,2-, 1,3- or 1,4-butylene, 1,3- or 1,5-pentylene, hexylenes, heptylenes, octylenes, decylenes, dodecylenes, tetradecylenes, hexadecylenes, octadecylenes, eicosylenes, 2,4,4-trimethylhexylene, 1,10-dialkyldecylenes, in which the alkyl preferably has 1 to 6 C atoms, substituted 1,11-undecylenes, such as are described, for example, in European Patent No. B-0,011,559, radicals of jeffamines, such as, for example,

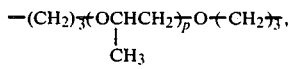

where p is 1 to 100, or —(CH$_2$)$_{\overline{3}}$(O(CH$_2$)$_4$)$_{\overline{p}}$O—(CH$_2$)$_{\overline{3}}$, where p is 1–100, dimethylenecyclohexane, xylylene and diethylenebenzene.

The aliphatic radicals interrupted by heterocyclic radicals can be, for example, those which are derived from N,N'-aminoalkylated hydantoins or benzimidazoles. Examples are N,N'-(γ-u-aminopropyl)-5,5-dimethyl-hydantoin or -benzimidazolone and those of the formula

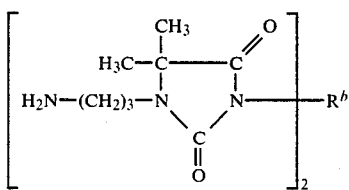

in which R$^b$ is alkylene with 1 to 12, preferably 1 to 4, C atoms, or

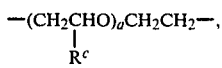

in which R$^c$ is a hydrogen atom or methyl and a is an integer from 1 to 20.

A divalent aliphatic radical X can also be a divalent radical containing siloxane groups. This can have the formula

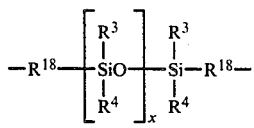

in which x is a rational number of at least 1, R$^3$ and R$^4$ are as defined above and R$^{18}$ is a divalent hydrocarbon radical, for example alkylene with 1 to 12, preferably 1 to 6, C atoms, cycloalkylene with preferably 5 or 6 ring carbon atoms or phenylene. R$^3$ and R$^4$ are preferably methyl or phenyl and x is preferably a number from 1 to 1,000, in particular 1 to 100 and especially 1–10. Examples of alkylene are ethylene, 1,3- or 1,2-propylene and 1,3- or 1,4-butylene. Diamines with this group X are described in U.S. Pat. No. 4,030,948. Other suitable diamines with a group X containing siloxane groups are described in U.S. Pat. No. 3,435,002 and European Pat. No. A-0,054,426.

Suitable substituents for the aliphatic radicals are, for example, hydroxyl, halide, such as F or Cl, or alkoxy with 1 to 6 C atoms.

A divalent cycloaliphatic radical X in formula I preferably contains 5 to 8 ring C atoms and is, in particular, mono- or dinuclear cycloalkylene which has 5 to 7 ring C atoms and is unsubstituted or substituted by alkyl, which preferably contains 1 to 4 C atoms. In a preferred embodiment, a cycloaliphatic radical X is one of the formula

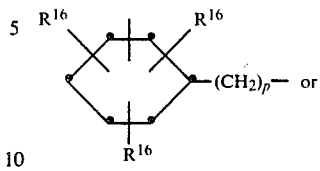

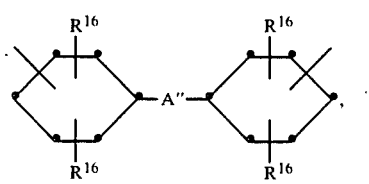

in which q is 0 or 1, the radicals R$^{16}$ independently of one another are hydrogen or alkyl with 1 to 6 C atoms and A" is a direct bond, —O—, —S—, —SO$_2$—, alkylene with 1 to 3 C atoms or alkylidene with 2 to 6 C atoms. R$^{16}$ is preferably ethyl or methyl, A" is preferably methylene, and the alkylidene preferably contains 2 or 3 C atoms, such as ethylidene or 1,1- or 2,2-propylidene.

Cycloalkylene X is, for example: 1,2- or 1,3-cyclopentylene, 1,2-, 1,3- or 1,4-cyclohexylene, cycloheptylene, cyclooctylene, methylcyclopentylene, methyl- or dimethylcyclohexylene, 3- or 4-methylenecyclohex-1-yl, 5-methyl-3-methylenecyclohex-1-yl, 3,3'- or 4,4'-biscyclohexylene, 3,3'-dimethyl-4,4'-biscyclohexylene, 4,4'-bis-cyclohexylene ether, -sulfone, -methane or -2,2-propane, or a radical of bis-aminomethyltricyclodecane, bis-aminomethylnorbornane or menthanediamine.

A cycloaliphatic radical X is particularly preferably 1,4- or 1,3-cyclohexylene, 2,2,6-trimethyl-6-methylenecyclohex-4-yl, methylenebis(cyclohex-4-yl) or methylenebis(3-methylcyclohex-4-yl).

Heterocyclic diamine radicals X are preferably derived from N-heterocyclic diamines, for example from pyrrolidine, indole, piperidine, pyridine or pyrrole, the N atom of which can be alkylated, for example methylated. An example is N-methyl-4-amino-5-aminomethyl-piperidine.

An araliphatic radical X preferably contains 7 to 30 C atoms. The aromatic groups are preferably substituted in the same manner as an aromatic radical X, including the preferred radicals, but are at least monosubstituted, preferably in the ortho-position relative to the N atom. The araliphatic radical contains, in particular, 8 to 26 C atoms. The aromatic radical in the araliphatic radical is preferably a phenyl radical. An araliphatic radical X is, in particular, aralkylene which is unsubstituted or substituted by alkyl on the aryl, the alkylene radical being linear or branched. In a preferred embodiment, the araliphatic radical has the formula

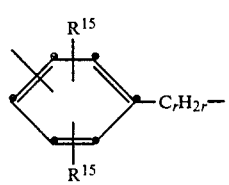

in which the radicals $R^{15}$ independently of one another are a hydrogen atom or, in particular, alkyl with 1–6 C atoms and r is an integer from 1 to 20.

The free bond is preferably in the m-position or p-position relative to the $C_rH_{2r}$ group, and one or both radicals $R^{15}$ are preferably bonded in the o-position relative to the free bond.

An araliphatic radical X is, for example: m- or p-benzylene, 3-methyl-p-benzylene, 3-ethyl-p-benzylene, 3,5-dimethyl-p-benzylene, 3,5-diethyl-p-benzylene, 3-methyl-5-ethyl-p-benzylene, p-phenylene-propylene, 3-methyl-p-phenylene-propylene, p-phenylenebutylene, 3-ethyl-p-phenylenepentylene or, in particular, a longer-chain phenylenealkylene radical described, for example, in European Patent No. A-0,069,062: 6-(p-phenylene)-6-methylhept-2-yl, 6-(3′-methyl-p-phenylene)-6-methylhept-2-yl, 6-(3′-ethyl-p-phenylene)-6-methylhept-2-yl, 6-(3′,5′-dimethyl-p-phenylene)-6-methylhept-2-yl, 11-(p-phenylene)-2,11-dimethyl-dodec-1-yl or 13-(p-phenylene)-1,12-dimethyltetradec-3-yl.

X can also be an aromatic radical in which two aryl nuclei, in particular phenyl, are linked via an aliphatic group. This radical preferably corresponds to the formula

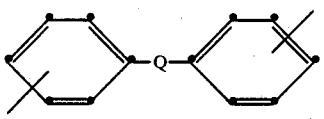

in which the free bonds are in the p-, m- or, in particular, o-position relative to the Q group and Q is $C_2$-$C_6$-alkylidene or $C_1$–$C_{12}$-, in particular $C_1$–$C_6$-alkylene, which can be interrupted by O or S. Examples of Q are ethylene, 1,2- or 1,3-propylene, butylene, —CH$_2$—O—CH$_2$—, —CH$_2$—S—CH$_2$— and —CH$_2$CH$_2$—O—CH$_2$CH$_2$—. The phenyl radicals can be substituted by groups such as fluorine, chlorine, carboxyl and esters thereof.

Examples are 4,4′-methylenebis-(o-chloroaniline), 5,5′-methylenebis(aminophenol), 4,4-methylenedianiline, 4,4′ethylidenedianiline, 4,4′-propylidenedianiline, 4,4′-methylenebis(3-carboxyaniline) and esters thereof.

Particularly preferred homo- and copolyimides are those with structural elements of the formula I in which X is substituted aromatic radicals. The substituent on the aromatic radical preferably contains 1 to 20, in particular 1–12 and especially 1–6, C atoms. The substituent is, in particular, cycloalkyl with 5 or 6 ring carbon atoms, linear or branched alkyl, alkoxy, alkylthio, hydroxyalkyl, hydroxyalkoxy or hydroxyalkylthio with 1 to 12, in particular 1–6, C atoms, akoxyalkyl, alkylthioalkyl with 2 to 12, in particular 2–6, C atoms, benzyl, trimethylene or tetramethylene. Preferred alkoxyalkyl is alkoxymethyl and preferred alkoxy is methoxy. Examples of the substituents are: methyl, ethyl, propyl, isopropyl, n-butyl, isobutyl, pentyl, hexyl, octyl, dodecyl, tetradecyl, eicosyl, methoxy, ethoxy, propoxy, butoxy, pentoxy, hexoxy, methoxymethyl, methoxyethyl, ethoxymethyl, propoxymethyl, butoxymethyl, benzyl, methylbenzyl, phenylethyl, methylthio, ethylthio, hydroxyethyl, methylthioethyl and hydroxyethylthio. Preferred radicals are methoxymethyl, ethoxymethyl, methyl, ethyl, n-propyl, i-propyl, trimethylene and tetramethylene, cyclopentyl and cyclohexyl. Especially preferred radicals are, in particular, methyl, and ethyl and i-propyl. The substituted aromatic radical can be a mononuclear or polynuclear, in particular dinuclear, radical, in particular a mono- or dinuclear phenylene radical. Mononuclear radicals can contain up to 4, preferably 2, substituents and dinuclear radicals can contain up to 4, preferably 1 or 2, substituents in each nucleus. It has been found that the photosensitivity of those homo- or copolyimides in which one or two substituents are bonded in the ortho-position relative to the N atom is particularly high. Substitution in the ortho-position is therefore preferred. The aromatic radical is preferably bonded in the meta- or para-position relative to the N atom. In a preferred sub-group, the substituent of the aromatic radical contains 1 to 20 C atoms as alkyl or alkoxy, 2 to 12 C atoms as alkoxyalkyl, 5 or 6 ring carbon atoms as cycloalkyl, 3 or 4 C atoms as alkylene and benzyl as aralkyl. The substituent is preferably alkyl with 1 to 4 C atoms, in particular isopropyl, ethyl and, especially, methyl.

A substituted aromatic radical X can contain 7 to 30, in particular 8 to 25, C atoms. The aromatic radical is preferably a pyridine radical, and in particular a hydrocarbon radical which is substituted by alkyl, alkoxyalkyl, alkoxy, trimethylene or tetramethylene. The aromatic radical can contain further substituents, for example halide, such as Cl or Br. In a preferred sub-group, the aromatic radicals are phenylene radicals as mononuclear radicals, and naphthylene or bisphenylene as dinuclear radicals.

A preferred sub-group of polyimides according to the invention are those in which a substituted aromatic radical X has the formulae VIII, VIIIa and/or VIIIb

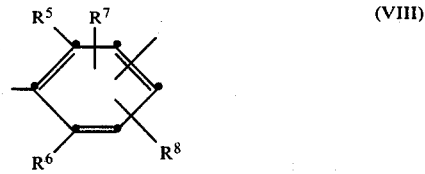

(VIII)

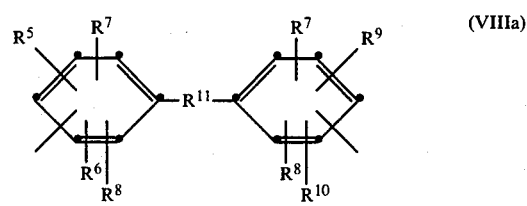

(VIIIa)

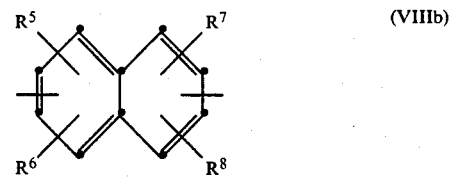

(VIIIb)

in which in formula VIII the free bonds are in the meta- or para-position relative to one another, in formula VIIIa the free bonds are preferably in the meta- or para-position relative to the $R^{11}$ group and $R^5$ and $R^6$ are bonded in the two ortho-positions relative to the free bond, and in formula VIIIb the free bonds are in the 2-, 3-, 6- and 7-position and $R^5$ and $R^6$ are in the two ortho-positions relative to the free bonds, $R^{11}$ is a direct bond, —O—, —S—, —SS—, —SO—, —SO$_2$—, —CO—, —COO—, —NH—, —N—alkyl-with 1 to 6 C atoms in the alkyl,

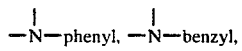

—CONH—, —CON-alkyl— with 1 to 6 C atoms in the alkyl, —CON—phenyl—, —CON—benzyl—,

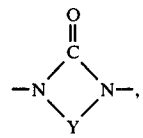

in which Y is

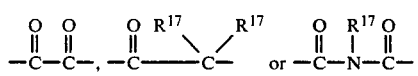

and $R^{17}$ is a hydrogen atom, $C_1$-$C_6$-alkyl or phenyl, linear or branched alkylene with 1 to 3 C atoms, alkylidene with 2 to 12 C atoms which is unsubstituted or substituted by Cl or F, cycloalkylidene with 5 or 6 ring carbon atoms, phenylene, phenylenedioxy or the group

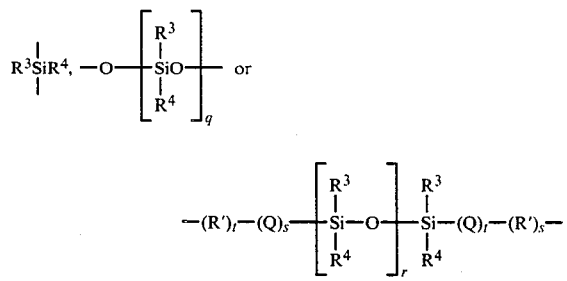

in which $R^3$ and $R^4$ are alkyl or alkoxy with 1 to 6 C atoms, phenyl, benzyl, phenoxy or benzyloxy, r is a number from 1 to 10, t is 0 or 1 and s is 0 or 1, and R' is —O— or —S— and Q is $C_1$-$C_6$-alkylene, and q is a numbeer from 1 to 100, $R^5$ and $R^6$ are alkyl, or alkoxy with 1 to 12 C atoms, alkoxyalkyl with 2 to 12 C atoms, cyclopentyl, cyclohexyl or benzyl, or in the formula VIII or VIIIa $R^5$ and $R^7$ are bonded in adjacent positions and together are trimethylene or tetramethylene, in which $R^6$ can also be a hydrogen atom, $R^7$ and R8 are a hydrogen atom or independently have the meaning of $R^5$ and $R^6$, and $R^9$ and $R^{10}$ are a hydrogen atom, or independently have the meaning of $R^5$ and $R^6$, or $R^7$ and $R^9$ in formula VIIIa together are trimethylene or tetramethylene. $R^5$ and $R^6$ are preferably alkyl with 1 to 6 C atoms, in particular methyl, ethyl, n-propyl or isopropyl. The free bonds in formula VIIIa are preferably in the meta- or, in particular, para-position relative to the $R^{11}$ group The alkyl in the $R^{11}$ radicals can be, for example, methyl, ethyl, propyl, isopropyl, n-butyl or pentyl. Alkylene $R^{11}$ is preferably ethylene or, in particular, methylene. Alkylidene $R^{11}$ preferably contains 2 to 6 C atoms. Examples are ethylidene, 2,2-butylidene, 2,2- or 3,3-pentylidene, hexafluoropropylidene and, in particular, 2,2-propylidene. Cycloalkylidene $R^{11}$ can be, for example, cyclopentylidene or, in particular, cyclohexylidene. The $R^{11}$ group is preferably a direct bond, —O—, —S—, —$SO_2$—, —CO—, alkylene or alkylidene. $R^{11}$ is particularly preferably a direct bond, —O— or, in particular, —CO— or —$CH_2$—. $R^3$ and $R^4$ are preferably alkyl, in particular methyl or phenyl. R' is preferably —O— and Q is preferably methylene or ethylene, q is preferably a number from 1 to 10 and r is a number from 1 to 20, in particular 1–10.

Another preferred group of substituted aromatic diamine radicals are those of the formula

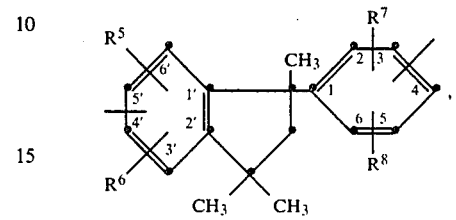

in which the free bond is in the 4'- or 5'-position and the other is in the 3-, 5- or, preferably, 4-position, $R^5$ and $R^6$ and/or $R^7$ and $R^8$ are in the ortho-positions relative to the free bond and are alkyl or alkoxy with 1 to 12 C atoms or alkoxyalkyl with 2 to 12 C atoms.

A particularly preferred sub-group of polyimides according to the invention are those in which X in formula I is a radical of the formula

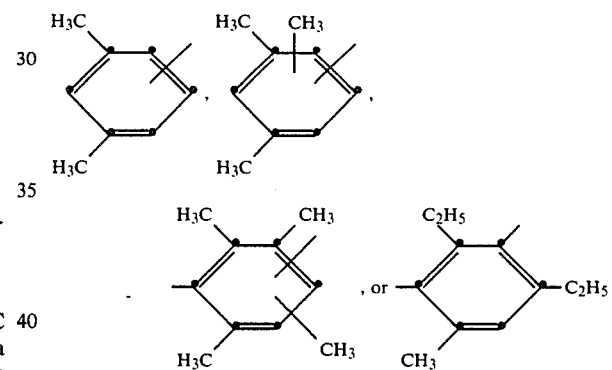

in which the free bonds are in the meta- or para-position relative to one another, or of the formula

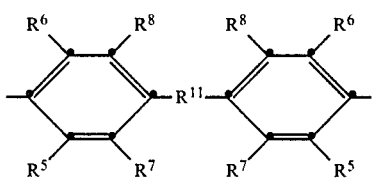

in which $R^5$ and $R^6$ indepdently are met , n-propyl or isopropyl and $R^7$ and $R^8$ are a hydrogen atom or have the meaning of $R^5$, or $R^5$ and $R^7$ together are trior tetramethylene and $R^6$ and $R^8$ are a hydrogen atom, and $R^{11}$ is a direct bond, $CH_2$, 2,2-propylidene or CO. Of these dinuclear radicals, those in which $R^5$,$R^6$,$R^7$ and $R^8$ are methyl are particularly preferred. Copolyimides which contain at least 2 different radicals of these formulae are another preferred embodiment of the invention.

Copolymides according to the invention contain at least two different structural elements, the number of different structural elements essentially depending on the desired properties and the field of application. They preferably contain 2 to 4 different structural elements, and the structural elements may differ only in the radical X of formula I. In a particularly preferred embodiment of such copolyimides, structural elements of ortho-disubstituted phenylenes, in particular 1,3-phenylenes, are present.

Examples of X are: 2-methyl-1,4-phenylene, 2,6-dimethyl-1,4- or -1,3-phenylene, 2,6-diethyl-1,4- or -1,3-phenylene, 2,6-dimethyl-5-chloro-1,4- or -1,3-phenylene, 2-methyl-6-ethyl-1,4- or -1,3-phenylene, 2-methyl-6-isopropyl1,4- or -1,3-phenylene, 2,6-diisopropyl-1,4- or -1,3-phenylene, 2,6-dimethoxy-1,4- or -1,3-phenylene, 2,6-diethoxy-1,4-or -1,3-phenylene, 2-methyl-6-methoxy-1,4- or -1,3-phenylene, 2,6-dibenzyl-1,4- or -1,3-phenylene, 2,6-dimethoxymethyl-1,4- or -1,3-phenylene, 2,5,6-trimethyl-1,4- or -1,3-phenylene, 2,5,6-triethyl-1,4- or -1,3-phenylene, 2,4,6-trimethyl1,3-phenylene, 2,3,5,6-tetramethyl-1,4-phenylene, 2,4,5,6-tetramethyl-1,3-phenylene, tetrahydro-1,4- or -1,3-naphthylene, and radicals of the formulae

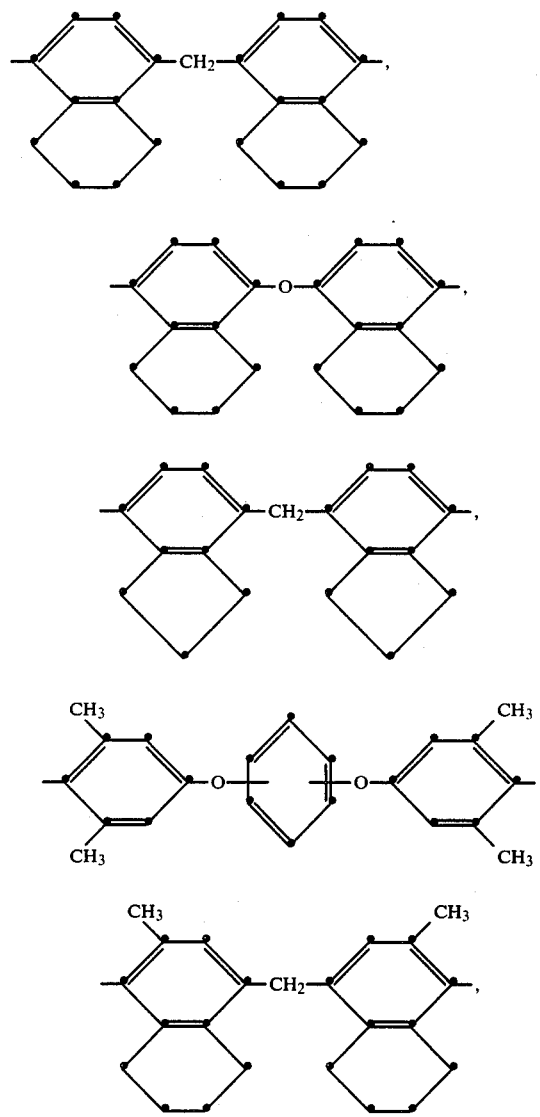

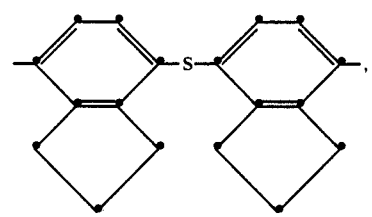

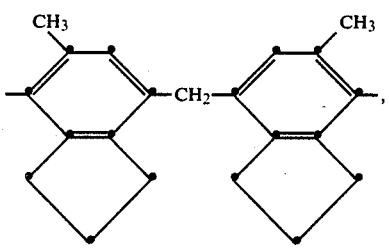

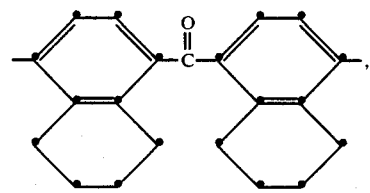

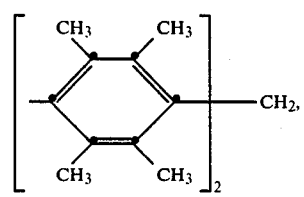

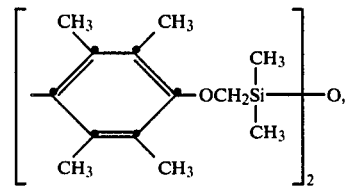

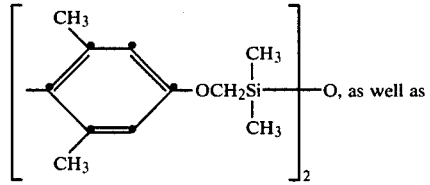

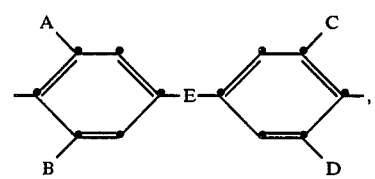

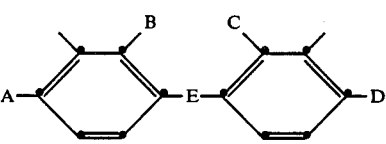

-continued

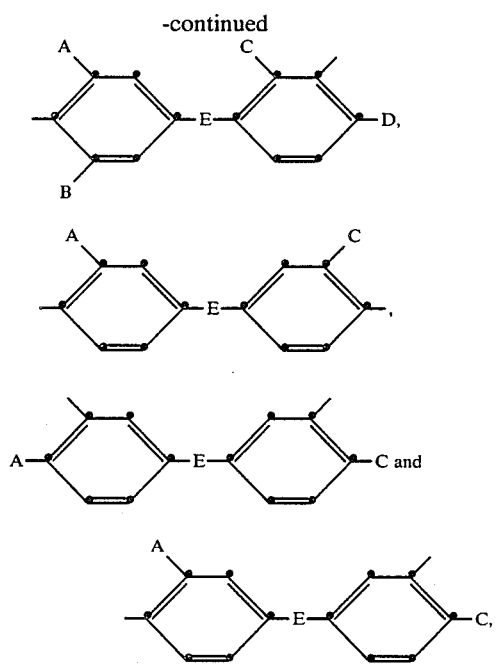

in which A, B, C, D and E are as defined in the following table. The free positions in the phenyl nuclei here can be occupied by one or two other substituents G or H in each nucleus, and G or H can have the meaning given for A in the following table:

| E | A | B | C | D |
|---|---|---|---|---|
| $CH_2$ | Methyl | Methyl | H | H |
| $CH_2$ | Methyl | Ethyl | H | H |
| $CH_2$ | Ethyl | Ethyl | H | H |
| $CH_2$ | Isopropyl | Isopropyl | H | H |
| $CH_2$ | Methoxymethyl | | H | H |
| $CH_2$ | Benzyl | Benzyl | H | H |
| $CH_2$ | Methyl | Methyl | Methyl | H |
| $CH_2$ | Ethyl | Ethyl | Ethyl | H |
| $CH_2$ | Isopropyl | Isopropyl | Methyl | Methyl |
| $CH_2$ | Methoxymethyl | | Methyl | H |
| $CH_2$ | Methyl | Ethyl | Methyl | H |
| $CH_2$ | Methoxymethyl | | | Methoxymethyl |
| $CH_2$ | Methyl | Methyl | Methyl | Methyl |
| $CH_2$ | Ethyl | Ethyl | Ethyl | Ethyl |
| $CH_2$ | Methyl | Methyl | Ethyl | Ethyl |
| $CH_2$ | Ethyl | Ethyl | Isopropyl | Isopropyl |
| $CH_2$ | Isopropyl | Isopropyl | Isopropyl | Isopropyl |
| $CH_2$ | Isopropyl | Isopropyl | Methyl | H |
| $CH_2$ | Methoxy | Methoxy | Methyl | Methyl |
| O | Ethyl | Methyl | H | H |
| O | Ethyl | Aethyl | H | H |
| O | Methyl | Methyl | Methyl | H |
| O | Methyl | Methyl | Methyl | Methyl |
| O | Methyl | Methyl | Ethyl | Ethyl |
| S | Methyl | Methyl | H | H |
| S | Ethyl | Ethyl | H | H |
| S | Methyl | Methyl | H | H |
| S | Methyl | Methyl | Methyl | Methyl |
| S | Ethyl | Ethyl | Ethyl | Ethyl |
| S | Methyl | Methyl | Ethyl | Ethyl |
| CO | Methyl | Methyl | Methyl | H |
| CO | Methyl | Methyl | H | H |
| CO | Methyl | Methyl | Methyl | Methyl |
| $SO_2$ | Methyl | Methyl | Ethyl | H |
| $SO_2$ | Methyl | Methyl | H | H |
| $SO_2$ | Methyl | Methyl | Methyl | Methyl |
| $SO_2$ | Ethyl | Ethyl | Methyl | Methyl |
| SO | Methyl | Methyl | Methyl | Methyl |
| SO | Methyl | Methyl | H | H |
| COO | Methyl | Methyl | H | H |
| COO | Methyl | Methyl | Methyl | Methyl |
| $CONCH_3$ | Methyl | Methyl | H | H |
| $NCH_3$ | Methyl | Methyl | Ethyl | Ethyl |
| $NCH_3$ | Methyl | Methyl | Methyl | Methyl |
| CONH | Methyl | Methyl | — | — |
| NH | Ethyl | Methyl | Ethyl | Methyl |
| NH | Methyl | Methyl | Methyl | Methyl |
| $Si(Methyl)_2$ | Methyl | Methyl | H | H |
| $Si(Phenyl)_2$ | Methyl | Methyl | Methyl | Methyl |
| $Si(OMethyl)_2$ | Ethyl | Ethyl | H | H |
| $Si(OPhenyl)_2$ | Methyl | Methyl | Methyl | Methyl |
| $-OSi(Methyl)_2O-$ | Methyl | Methyl | Methyl | Methyl |
| Ethylene | Methyl | Methyl | H | H |
| Ethylene | Methyl | Methyl | Methyl | Methyl |
| Ethylene | Ethyl | Ethyl | H | H |
| Ethylene | Methyl | Methyl | Ethyl | Ethyl |
| Phenylene | Methyl | Methyl | Methyl | Methyl |
| Phenylene | Ethyl | Ethyl | H | H |
| $(CH_3)_2C=$ | Methyl | Ethyl | Methyl | Ethyl |
| $(CH_3)_2C=$ | Methyl | Methyl | Methyl | Methyl |
| $(CF_3)_2C=$ | Methyl | Methyl | Methyl | Methyl |
| direct bond | Methyl | Methyl | H | H |
| direct bond | Methyl | Ethyl | Methyl | Ethyl |
| direct bond | Methyl | Ethyl | Methyl | H |
| direct bond | Ethyl | Ethyl | Ethyl | Ethyl |
| direct bond | Methoxy | Methoxy | Methoxy | Methoxy |
| direct bond | Isopropyl | Isopropyl | H | H |
| direct bond | Methoxy—methyl | Methoxy—methyl | Methoxy—methyl | Methoxy—methyl |

In another preferred embodiment, a substituted aromatic radical X has the formula IX

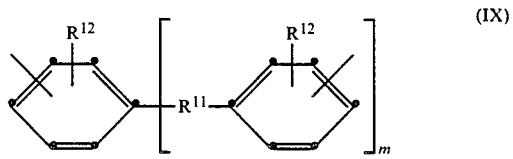

in which m is 0 or 1, the free bonds are in the meta- or, preferably, in the ortho-position relative to the $R^{12}$ group, $R^{11}$ is as defined for formula VIIIa and $R^{12}$ has the same meaning as $R^5$. The free bonds are preferably in the para- or, in particular, meta-position relative to the $R^{11}$ group.

A preferred sub-group are arylene radicals of the formulae Ixa, Ixb and Ixc

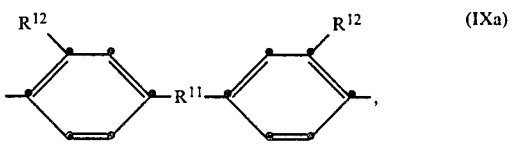

-continued

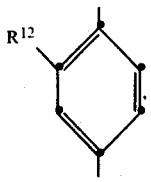
(IXc)

in which R¹¹ is a direct bond, —O—, —CO— or —CH₂— and R¹² is methyl, ethyl, isopropyl, methoxy, ethoxy or a hydrogen atom.

Examples of diamines H₂N-X-NH₂ with an aromatic radical of one of the formulae IX are: 4,4'-methylenebis-(3-methylaniline), 4,4'-methylenebis-(2-ethylaniline), 4,4'-methylenebis-(2-methoxyaniline), 5,5'-methylenebis-(2-aminophenol), 4,4'-methylenebis-(2-methylaniline), 4,4'-oxybis-(2-methoxyaniline), 4,4'-thiobis-(2-methylaniline), 4,4'-thiobis-(2-methoxyaniline), 4,4'-sulfonylbis-(2-methylaniline), 4,4'-sulfonylbis-(2-ethoxyaniline), 3,3'-dimethyl-4,4'-diaminobenzophenone, 3,3'-dimethoxy-4,4'-diaminobenzophenone, 4,4'-methylenedianiline, 3,3'-dimethylbenzidine, 3,3'-dimethoxybenzidine, diaminotoluene and 5-amino-1-(4-aminophenyl)-1,3,3-trimethylindane.

A diamine radical X' other than X can be, for example, phenylene which is unsubstituted or substituted by halogen or C₁-C₄-acyl, or bisphenylene of the formula

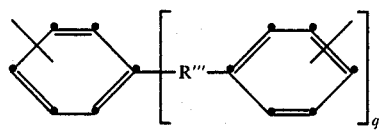

in which q is 0 or 1 and R''' is a direct bond, —O—, —S—, —SS—, —SO—, —SO₂—, —CO—,

—COO—, —NR²—, —NH—, —CONH—, —SiR³R⁴— or —OSi(R³R⁴)O—, and R², R³ and R⁴ are C₁-C₆-alkyl, phenyl or benzyl and R³ and R⁴ are also C₁-C₆-alkoxy, phenoxy or benzyloxy. The free bonds are preferably in the para-position or, in particular, in the meta-position relative to the R''' group. Examples of such diamines are: 3,3'-dichlorobenzidine, 3,3'-sulfonyldianiline, 4,4'- or 3,3'-diaminobenzophenone, 1,5-diaminonaphthalene, bis-(4- or 3-aminophenyl)-dimethylsilane, bis-(4- or 3-aminophenoxy)-dimethylsilane, N-bis(4-aminophenyl)-N-methyl- or -N-phenylamine, 4,4'-oxybis(2-chloroaniline), 5,5'-oxybis(2-aminophenol), 4,4'-thiobis(aniline), 4,4'-sulfonylbis(2-chloroaniline), 5,5'-sulfonylbis(2-aminophenol), 3,3'-dichloro-4,4'-diaminobenzophenone, 4,4'- or 3,3'-diaminobisphenyl, m-phenylenediamine, p-phenylenediamine, 4,4'-oxydianiline, 4,4'- or 3,3'-thiodianiline, 4,4'-sulfonyldianiline and 3,3'-dicarboxybenzidine.

It is known that some aliphatic and aromatic diamines, for example phenylenediamine or di(aminophenyl)-methane, can promote the insolubility of polyimides. Such diamines are therefore preferably employed in smaller amounts. In this case, in particular, the structural elements of the formula I are present to the extent of at least 50 mol %, in particular 80 mol % and especially 90 mol %.

The polyimides according to the invention have average molecular weights (weight-average Mw) of preferably at least 2,000, in particular at least 5,000. The upper limit essentially depends on properties which determine the processability, such as, for example, their solubility. It can be up to 500,000, preferably up to 100,000 and in particular up to 60,000. The compounds can furthermore be random polyimides or block polyimides. They are prepared by customary processes in the devices envisaged for this purpose.

The present invention furthermore relates to a process for the preparation of the polyimides according to the invention, which comprises subjecting at least 0.1 mol % of at least one tetracarboxylic acid of the formula X

(X)

by itself or together with not more than 99.9 mol %, based on the tetracarboxylic acids, of at least one tetracarboxylic acid of the formula Xa, and/or aminodicarboxylic acid of the formula Xb or polyimide-forming derivatives thereof,

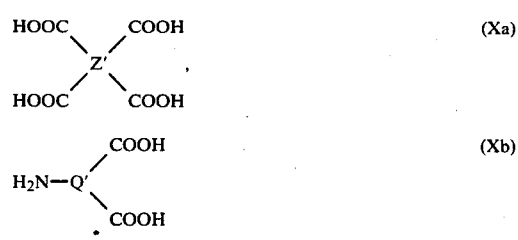
(Xa)

(Xb)

to polycondensation with at least 0.1 mol %, based on the diamines, of at least one diamine of the formula XI

(XI)

by themselves or together with not more than 99.9 mol % of at least one diamine of the formula XIa

(XIa)

in a manner which is known per se, and subsequently cyclising the product.

The diamines of the formulae XI and XIa are known or can be prepared by known processes. Si-containing diamines are described in U.S. Pat. No. 3,435,002 and European Patent No. A-0,054,426. Diamines with

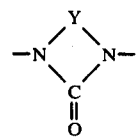

group can be prepared from the diisocyanates described in German Patent No. A-2,318,170. Alkyl- or cycloalkyl-substituted, in particular ethyl- or propyl-substituted, diamines are accessible by alkylation of unsubstituted or partly substituted aromatic diamines with alkenes or cycloalkenes (c.f. U.S. Pat. No. 3,275,690). Polynuclear, in particular dinuclear, aromatic diamines are obtainable via condensation of corresponding monoamines with aldehydes or ketones.

The tetracarboxylic acids of the formula Xa and aminedicarboxylic acids of the formula Xb are also known. Tetracarboxylic acids with a structural element of the formula VII are described in Macromol. Chem. 183, 1615–1622 (1982).

4,4'-Ketobis-(naphthalene-1,2-dicarboxylic acid) is obtainable by reacting 2 moles of 1,2-dimethylnaphthalene with $COCl_2$ in the presence of $AlCl_3$ and subsequently oxidising the 4,4'-ketobis(1,2-dimethylnaphthalene) formed with $HNO_3$ to give the tetracarboxylic acid. This tetracarboxylic acid can be partly hydrogenated to 4,4'-keto-(tetrahydronaphthalene-1,2-dicarboxylic acid). The hydrogenation can also be carried out with 4,4'-ketobis(1,2-dimethylnaphthalene) before the oxidation.

Tetracarboxylic acids with structural elements of the formula IV are known in some cases.

Anthraquinonetetracarboxylic acids are described, for example, in U.S. Pat. No. 3,702,318 and CA No. 100,1006119a (1984).

Hydrogenation of the keto groups in anthraquinonetetracarboxylic acids with, for example, $NaBH_4$ gives the corresponding dihydroxy compound, which can be converted into anthronetetracarboxylic acid by treatment with hydrochloric acid under reflux. The $CH_2$ group of the anthronetetracarboxylic acid can be alkylated in a known manner and thus converted into the $CRR^1$ group in formula IV.

To prepare fluorenonetetracarboxylic acid, for example, it is possible to dimerise 3,4-dimethyl-magnesium bromide in the presence of $CuCl_2$ and to react the 3,3',4,4'-tetramethylbiphenyl formed with $COCl_2$ in the presence of $AlCl_3$ to give tetramethylfluorenone, which can be oxidised in a known manner with, for example, $HNO_3$ to give the tetracarboxylic acid.

Xanthonetetracarboxylic acid is obtained by first reacting 3,3',4,4'-tetramethylphenyl ether with $CCl_4$ in the presence of $AlCl_3$ and then hydrolysing the product with dilute HCl to give 2,3,6,7-tetramethylxanthone, which is oxidised to the tetracarboxylic acid in the customary manner, for example with $HNO_3$.

Tetracarboxylic acids with structural elements of the formula IV in which Y is S, SO, $SO_2$ or NR are obtainable in the following way: 1-chloro-3,4-dimethylbenzene is reacted with oxalyl chloride in the presence of $AlCl_3$ to give bis-(5-chloro-2,3-dimethylphenyl) ketone.

Oxidation with 20% $HNO_3$ gives

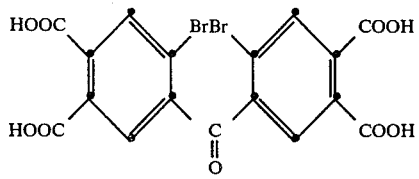

Reaction with $Na_2S$ after the esterification gives the thioxanthonetetracarboxylic acid, which can be oxidised in a known manner to give the sulfoxide or sulfone. Reaction with $RNH_2$ gives the acridonetetracarboxylic acids.

The present invention also relates to tetracarboxylic acids of the formula XII

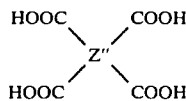

(XII)

in which Z" is a radical of the formulae XIIIa to XIIIc

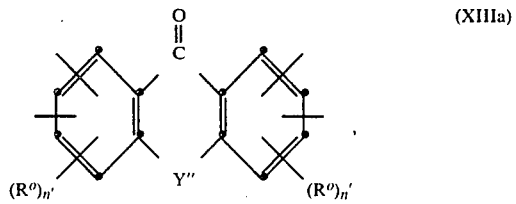

(XIIIa)

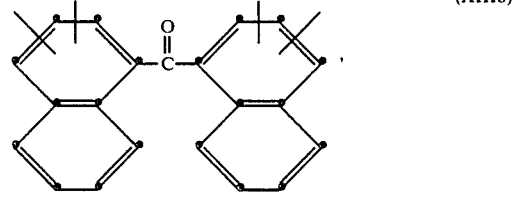

(XIIIb)

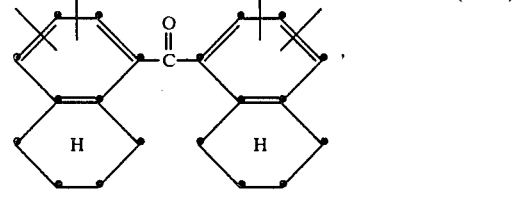

(XIIIc)

in which the free bonds are in the ortho-position relative to one another and Y" is a direct bond, $-CH_2-$, $-CH_2-CH_2-$, $-O-$, $-S-$, $-SO-$, $-SO_2-$, $-NR-$ or $-CRR^1-$, in which R is a hydrogen atom, $C_1-C_{10}$-alkyl, phenyl, naphthyl or phenyl-$(C_aH_{2a})$-, where a is 1–4, and $R^1$ has the meaning of R, with the exception of a hydrogen atom, and $R^o$ is $C_1-C_{10}$-alkyl, halogen, $-CN$, $-NO_2$, $C_1-C_{12}$-alkoxy, phenoxy, naphthoxy or phenyl$(C_aH_{2a})$-, where a is 1–4, and n' is 0, 1 or 2, and the acid derivatives.

Acid derivatives are, for example, the anhydrides, esters, amides and halides, in particular chlorides.

Preferred tetracarboxylic acids of the formula XII are those in which, in the formulae XIIIa to XIIIc, the free bonds are in the meta- or para-position relative to the CO group, n' is O and Y" is a direct bond, $-CH_2-$, $-O-$, $-S-$, $-SO-$ or $-SO_2-$.

The preparation of the polyimides is advantageously carried out in solution; suitable inert solvents are listed below. The reaction temperatures can be $-20°$ to $300°$ C.

In detail, a procedure is advantageously followed in which the tetracarboxylic dianhydride and diamine are first reacted to form a polyamic acid precursor and this polyamic acid is then cyclised, water being detached. Cyclisation can be carried out under the influence of heat. The cyclisation is advantageously carried out under the influence of dehydrating agents, for example carboxylic anhydrides, such as acetic anhydride. The polyimides can then be isolated by customary processes, for example by removal of the solvent or precipitation by addition of a non-solvent.

Another preparation method comprises reacting the tetracarboxylic dianhydride with a diisocyanate in one stage to give the polyimide.

The polyimides according to the invention are soluble in various solvents, if necessary with warming, and they have high glass transition points. They are outstandingly suitable for the production of films and protective coatings, and coating agents from a solution of the polyimide in a solvent can be used. The present invention also relates to the use of the polyimides according to the invention for the production of protective coatings and films.

To prepare the coated material, the polymer or a mixture thereof is advantageously dissolved in a suitable organic solvent, if necessary with warming. Suitable solvents are, for example, polar aprotic solvents, which can be used by themselves or as mixtures of at least two solvents. Examples are: ethers, such as dibutyl ether, tetrahydrofuran, dioxane, methylene glycol, dimethylethylene glycol, dimethyldiethylene glycol, diethyldiethylene glycol and dimethyltriethylene glycol, halogenated hydrocarbons, such as methylene chloride, chloroform, 1,2-dichloroethane, 1,1,1-trichloroethane and 1,1,2,2-tetrachloroethane, carboxylic acid esters and lactones, such as ethyl acetate, methyl propionate, ethyl benzoate, 2-methoxyethyl acetate, $\gamma$-butyrolactone, o-valerolactene and pivalolactone, carboxylic acid amides and lactams, such as formamide, acetamide, N-methylformamide, N,N-dimethylformamide, N,N-diethylformamide, N,N-dimethylacetamide, N,N-diethylacetamide, $\gamma$-butyrolactam, $\epsilon$-caprolactam, N-methylpyrrolidone, N-acetylpyrrolidone, N-methylcaprolactam, tetramethylurea and hexamethylphosphoric acid triamide, sulfoxides, such as dimethyl sulfoxide, sulfones, such as dimethyl sulfone, diethyl sulfone, trimethylene sulfone and tetramethylene sulfone, amines, such as trimethylamine, triethylamine, N-methylpiperidine and N-methylmethylmorpholine, and substituted benzenes, such as chlorobenzene, nitrobenzene, phenols or cresols.

Undissolved constituents can be removed by filtration, preferably pressure filtration. The concentration of polymer in coating agents thus obtained is preferably not more than 50% by weight, in particular not more than 30% by weight and especially not more than 20% by weight, based on the solution.

Other customary additives which do not adversely influence the photosensitivity can be incorporated during preparation of the solution. Examples of these are matting agents, flow control agents, finely divided fillers, flame-proofing agents, fluorescent brighteners, antioxidants, light stabilisers, stabilisers, dyes, pigments, adhesion promoters and antihalo dyes, such as are described, for example, in U.S. Pat. No. 4,349,619.

The coating agent can be applied to suitable substrates or carrier materials by means of customary methods, such as immersion, brushing and spraying processes, or whirler, cascade and curtain coating, and adhesion promoters or adhesive layers can also be used. Suitable substrates are, for example, plastics, metals and metal alloys, semi-metals, semiconductors, glass, ceramics and other inorganic materials, for example $SiO_2$ and $Si_3N_4$. The solvent is then removed, if necessary by warming and if necessary in vacuo. Tack-free, dry and uniform films are obtained. Depending on the use, the films applied can have coating thicknesses of up to about 500 $\mu$m or more, preferably from 0.5 to 500 $\mu$m and in particular from 1 to 50 $\mu$m.

It has been found that the polyimides according to the invention are autophotocrosslinkable and can be crosslinked under the influence of radiation.

Since the photosensitivity increases as the content of structural elements of the formula I increases, a content of at least 50 mol %, preferably at least 80 mol % and in particular at least 90 mol %, is advantageous.

Protective films of such polyimides can be further modified by the influence of radiation, so that, for example, increased heat stabilities are possible. There is also the possibility of employing such polyimides as photographic recording material for relief images. As a result of direct crosslinking under the influence of radiation, additives such as sensitisers can be avoided and the protective coatings and images have excellent electrical properties. The protective coatings and images are furthermore distinguished by their high heat stability and by only little or no shrinkage when exposed to heat, which has considerable advantages during use, because virtually no distortion of imaged structures is observed.

The invention also relates to coating agents containing such a radiation-sensitive polyimide in solution, a carrier material coated with such polyimides and the use of this material for the production of protective coatings and photographic relief images. The coating thickness for this use is preferably 0.5 to 100 $\mu$m, in particular 1 to 50 $\mu$m and especially 1-10 $\mu$m.

Photostructuring or photocrosslinking can be caused by high-energy radiation, for example by light, in particular in the UV range, or by X-rays, laser light, electron beams and the like. The material according to the invention is outstandingly suitable for the production of protective films and passivating lacquers and as photographic recording material for heat-stable relief images.

Fields of use are, for example, protective, insulating and passivating varnishes in electrical engineering and electronics, photomasks for electronics, textile printing and the graphics industry, etch resists for the production of printed circuits and printed circuit boards and integrated circuits, relays for the production of X-ray masks, solder-stopping varnishes, dielectrics for multi-layer circuits and structural elements for liquid crystal display units.

Protective films are produced by direct exposure to light, the exposure times essentially depending on the coating thicknesses and the photosensitivity.

Photographic production of the relief structure is effected by image-wise exposure to light through a photomask and subsequent development, removing the non-exposed portions, with a solvent or a solvent mixture, after which, if appropriate, the image produced can be stabilised by after-treatment with heat.

The invention also relates to such a process for the application of relief structures. Suitable developers are, for example, the abovementioned solvents.

The polymer layer of the material according to the invention has a photosensitivity which is sufficient for many application purposes and is in some cases high, and it can be photocrosslinked directly. The protective films and relief images are distinguished by a high adhesive strength and resistance to heat, mechanical stresses and chemicals. Only slight shrinkage is observed during after-treatment with heat. Additives to produce or increase photosensitivity can furthermore be avoided. The material is stable on storage, but is advantageously to be protected from the influence of light.

The following examples illustrate the invention in more detail.

EXAMPLE a

Preparation of xanthonetetracarboxylic acid dianhydride

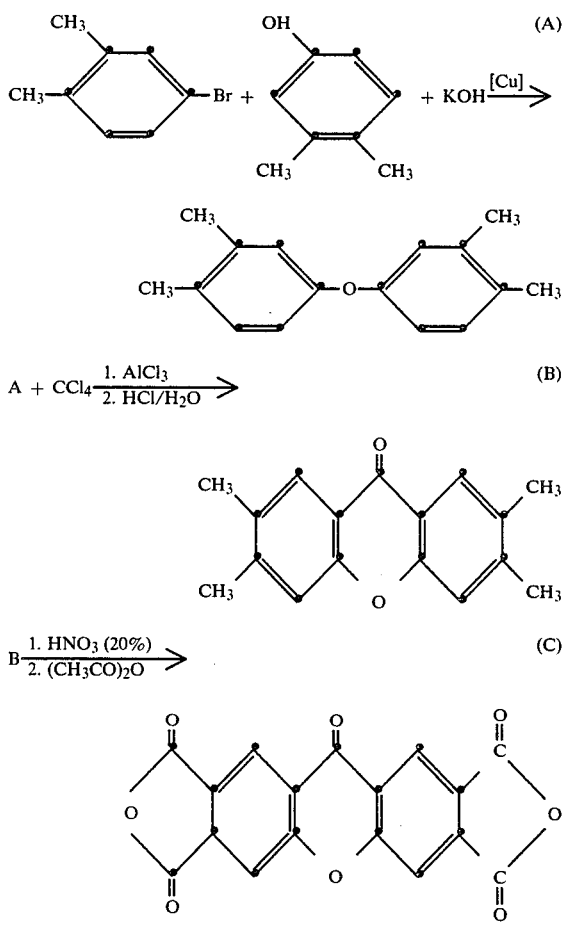

Preparation of A

A mixture of 165 g of 4-bromo-o-xylene, 122 g of 3,4dimethylphenol, 66 g of KOH and 10 g of Cu powder is heated to 170° C. in a flask and kept at this temperature overnight. The following morning, a further 10 g of Cu powder are added and the mixture is kept at 200° C. until about 10 ml of $H_2O$ have distilled off and the mixture solidifies. After a further 2 hours at 240° C., the mixture is cooled, water is added and the mixture is extracted with chloroform. After distilling off the solvent, the residue is distilled. 127 g of A are thereby obtained with a boiling point of 175°–178° C. under 18.2 mbar.

| | Elemental analysis: | |
|---|---|---|
| | calculated | found |
| C | 84.92 | 85.04 |
| H | 8.02 | 7.97 |
| O | 7.07 | 7.25 |

Preparation of B 22.6 g of A, dissolved in $CCl_4$, are slowly added dropwise to a mixture of 26.6 g of $AlCl_3$ and 50 ml of $CCl_4$ at room temperature. Whilst the evolution of HCl starts, the temperature increases to 40° C. After 3 hours, the reaction mixture is poured onto ice-water and diluted with $CHCl_3$ and the organic phase is separated off. After distilling off the solvent, 250 ml of 15% hydrochloric acid are added to the residue and the mixture is refluxed for 24 hours.

The solid product is filtered off, washed with water and then stirred with ether. After renewed filtration, the residue is dried and, without further purification, employed for the preparation of C.

Preparation of C 15 g of B are kept at 180° C. in a stirred autoclave together with 700 ml of 20% nitric acid for 10 hours. The cooled solution is evaporated to dryness and the residue (18.2 g) is refluxed with 400 ml of acetic anhydride for 24 hours. The acetic acid formed and the excess acetic anhydride are distilled off and the residue is sublimed at 300° under a high vacuum (<1 mbar).

| | Elemental analysis: | |
|---|---|---|
| | calculated | found |
| C | 60.73 | 60.10 |
| H | 1.20 | 1.16 |
| O | 38.07 | 37.92 |

EXAMPLE B

Preparation of thioxanthonetetracarboxylic acid dianhydride

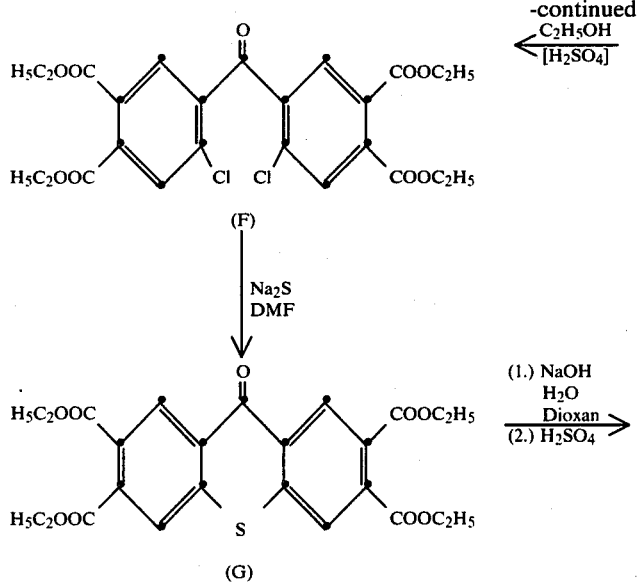

(F)

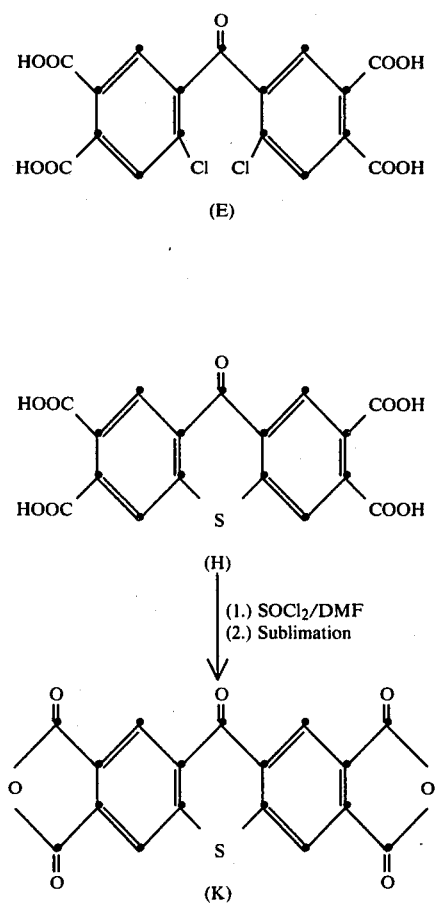

Preparation of D 146 g of AlCl₃ are added to a solution of 140 g of 4-chloro-o-xylene and 68 g of oxalyl chloride in 500 ml of CS₂ at 0°–5°C. in the course of 2 hours, with stirring. After 20 hours, the mixture is poured onto ice and extracted with 600 ml of CHCl₃. The extract is washed with water, dried and evaporated completely. Recrystallisation of the residue from diisopropyl ether gives 103.8 g of 2,2'-dichloro-4,4',5,5'-tetramethylbenzophenone (D). Melting point: 148°–149° C.

| Elemental analysis: | | | |
|---|---|---|---|
| calculated | | found | |
| C | 66.46% | C | 66.8% |
| H | 5.25% | H | 5.5% |
| O | 5.21% | O | 5.2% |
| Cl | 23.08% | Cl | 23.1% |

Preparation of E 76 g of D, suspended in 1.5 l of 20% nitric acid, are warmed at 180° C. in a tantalum autoclave for 24 hours. After cooling, the mixture is filtered and the solid residue is washed with a large amount of ice-water and dried. 68 g of tetracarboxylic acid (E) are obtained and are subsequently processed without further purification.

Preparation of F 68 g of E are esterified by refluxing E in 600 ml of ethanol and 15 ml of concentrated H₂SO₄ for 25 hours. After customary working up, the tetraethyl ester (F) is purified by column chromatography on silica gel (elution with toluene/CH₂Cl₂ 1:1 +2% of diethyl ether) and then recrystallised twice from diisopropyl ether. 41.8 g of F are thereby obtained. Melting point: 95°–96° C.

| Elemental analysis: | | | |
|---|---|---|---|
| calculated | | found | |
| C | 55.57% | C | 55.6% |
| H | 4.49% | H | 4.4% |
| O | 26.70% | O | 26.6% |
| Cl | 13.15% | Cl | 13.1% |

Preparation of G

A mixture of 26.9 g of F, 7.8 g of anhydrous sodium sulfide and 100 ml of dimethylformamide is warmed at 120° C. under an inert gas for 1 hour and then poured onto 800 ml of ice-water. The product which has precipitated out is filtered off and recrystallised from diisopropyl ether. 31.7 g of G are thereby obtained. Melting point: 108°–109° C.

| Elemental analysis: | | | |
|---|---|---|---|
| calculated | | found | |
| C | 59.99 | C | 59.9 |
| H | 4.83 | H | 4.9 |
| O | 28.77 | O | 28.7 |
| S | 6.41 | S | 6.4 |

Preparation of H 20 g of tetraethyl ester (G) are hydrolysed to the tetracarboxylic acid by first warming the substance in a mixture of 200 ml of 2 N NaOH and 50 ml of dioxane for 5 hours and then acidifying the mixture with dilute $H_2SO_4$. The tetracarboxylic acid which has precipitated out is filtered off (H) and dried. 16.5 g of H are obtained, and are subsequently processed without further purification.

Preparation of K 10.9 g of tetracarboxylic acid (H) are converted into the dianhydride (K) by treating with a mixture of 60 ml of dimethylformamide and 13.32 g of thionyl chloride at room temperature for 20 hours. The dianhydride is precipitated out by addition of 100 ml of toluene and filtered off. The dried substance is purified by sublimation under a high vacuum at 350° C. 7.4 g of dianhydride (K) are obtained.

| Elemental analysis: | | | |
|---|---|---|---|
| calculated | | found | |
| C | 57.96 | C | 57.7 |
| H | 1.15 | H | 1.3 |
| O | 31.79 | O | 31.7 |
| S | 9.1 | S | 8.9 |

EXAMPLE c a) Thioxanthone-10-oxide-2,3,6,7-tetracarboxylic acid tetraethyl ester 100 ml of a solution of peroxytrifluoroacetic acid in methylene chloride (according to *A. S. Pagano and W. G. Emmons,* Organic Syntheses Coll. Vol. V, 367 (1973)) are added dropwise to a stirred solution of thioxanthone-2,3,6,7-tetracarboxylic acid tetraethyl ester (20 g, according to Example b) in 200 ml of methylene chloride at −30° C. to −40° C. in the course of one hour. After the mixture has been stirred at −20° C. for 30 minutes, it is poured onto ice-water and the organic phase is separated off, washed with 5% sodium carbonate solution and water, dried with magnesium sulfate and evaporated. The residue (20 g) is separated by column chromatography on silica gel. Using methylene chloride/ethyl acetate =20:1, 15.2 g of the 10,10-dioxide, $R_f$ value 0.58, are first eluted and 4.8 g of the 10-oxide, $R_f$ value 0.3, are then eluted.

Melting point: 154°–155° C.

| Elemental analysis: | | | |
|---|---|---|---|
| calculated | | found | |
| C | 58.13% | C | 58.0% |
| H | 4.68% | H | 4.9% |
| O | 30.97% | O | 31.2% |
| S | 6.21% | S | 6.1% | b) Thioxanthone-10-oxide-2,3,6,7-tetracarboxylic acid 80 ml of 2 N sodium hydroxide solution are added to a solution of 4 g of tetraethyl ester according to a) in 20 ml of dioxane. After stirring at 60° C. for 4.5 hours, the mixture is cooled to room temperature and extracted with ethyl acetate. Drying (magnesium sulfate) and evaporation of the organic phase gives 3.3 g of crude tetracarboxylic acid, which is further reacted without purification.

c) Thioxanthone-10-oxide-2,3,6,7-tetracarboxylic acid bis-anhydride

Method A 0.15 ml of thionyl chloride is added to a solution of 400 mg of tetracarboxylic acid according to b) in 3 ml of dimethylformamide. After the mixture has been stirred at room temperature for 20 hours, 5 ml of toluene are added and the solvent is evaporated off in vacuo. The residue is dried at 50° C./0.026 mbar, triturated with 1 ml of dioxane and filtered off. Drying of the material on the filter (50° C./0.026 mbar) gives 130 mg of the bis-anhydride. Infrared spectrum (suspension in Nujol): bands with maxima at 1,885 cm$^{-1}$ and 1,773 cm$^{-1}$.

Method B 50 mg of tetracarboxylic acid according to b) are suspended in 20 ml of xylene. The suspension is warmed in a heating bath of 140° C. for 2 hours, with stirring, and distilled slowly. The undissolved material is filtered off and the filtrate is cooled and evaporated in vacuo. Yield: 32 mg of bis-anhydride.

d) Solution of thioxanthone-10-oxide-2,3,6,7-tetracarboxylic acid-tetra-(trimethylsilyl) ester in toluene 100 mg of N,O-bis-(trimethylsilyl)-acetamide are added to a suspension of 100 mg of tetracarboxylic acid according to b) in 25 ml of toluene. After brief stirring (about 5 min), a clear solution of tetra-(trimethylsilyl) ester forms, which can be used directly for polycondensation reactions.

EXAMPLE d

Thioxanthone-10,10-dioxide-2,3,6,7-tetracarboxylic acid

Method A a) Thioxanthone-10,10-dioxide-tetracarboxylic acid tetraethyl ester 19.5 ml of a solution of peroxytrifluoroacetic acid in methylene chloride (according to *A. S. Pagano and W. G. Emmons,* Organic Syntheses Coll. Vol. V, 367 (1973)) are added dropwise to a stirred solution of 3 g of thioxanthone-2,3,6,7-tetracarboxylic acid tetraethyl ester according to Example b in 60 ml of methylene chloride at 0°–5° C. The mixture is refluxed for 3 hours, cooled and washed with 5% sodium carbonate solution and with water. Evaporation of the dried (magnesium sulfate) organic phase and trituration of the residue (4.5 g) with 10 ml of diisopropyl ether gives 3.1 g of the 10,10-dioxide.

Melting point: 136°–137° C.

| Elemental analysis: | | | |
|---|---|---|---|
| calculated | | found | |
| C | 56.38% | C | 56.4% |
| H | 4.54% | H | 4.7% |
| O | 33.05% | O | 33.1% |
| S | 6.02% | S | 6.0% | b) Thioxanthone-10,10-dioxide-2,3,6,7-tetracarboxylic acid 200 ml of 2 N sodium hydroxide solution are added to a solution of 16 g of tetraethyl ester according to a) in 50 ml of dioxane. After stirring at 60° C. for 7 hours, the mixture is cooled, rendered acid with 10% sulfuric acid and extracted five times by shaking with 150 ml of ethyl acetate each time. Drying of the organic phase with magnesium sulfate and evaporation gives 10.9 g of tetracarboxylic acid.

c) Method B

A suspension of 1 g of thioxanthone-2,3,6,7-tetracarboxylic acid according to Example b in 50 ml of 20% nitric acid is warmed at 180° C. in a closed glass tube, with addition of a tantalum body, for 24 hours. Evaporation of the solution, dissolving of the residue in 50 ml of water, addition of 100 mg of active charcoal, filtration and evaporation of the filtrate give 1.1 g of crude 10,10-dioxide.

EXAMPLE e:

2,3,6,7-Tetracarboethoxy- and 1,2,6,7-tetracarboethoxy-fluorenone

Method A (a) 3,3',4,4'-Tetramethyl-biphenyl

A solution of 13.7 g of 4-bromo-o-xylene in 50 ml of dry tetrahydrofuran is added dropwise to a suspension of magnesium filings (1.95 g) in 50 ml of dry tetrahydrofuran in the course of 1 hour. After refluxing in an argon atmosphere for 2 hours, the mixture is cooled to room temperature and 9.4 g of anhydrous copper(II) chloride are added in portions. The mixture is poured onto ice-water and extracted twice with 100 ml of diethyl ether each time. The organic phase is washed with 2 N hydrochloric acid and saturated sodium chloride solution. Drying with magnesium sulfate, evaporation and crystallisation of the residue from ethanol gives 2.9 g of biphenyl.

Melting point: 74°–76° C.

Mass spectrum: m/e=210 (100%, M+)

b) 2,3,6,7-Tetramethyl- and 1,2,6,7-tetramethyl-fluorenone 35.6 g of anhydrous aluminium chloride are added in portions to a solution of 20 g of biphenyl according to a) and 14 g of phosgene in 130 ml of carbon disulfide at −10° C. to 0° C. in the course of 2 hours. After stirring at room temperature for 15 hours, the mixture is refluxed for 2 hours, poured onto ice-water and extracted with 1.5 l of chloroform. The residue from the organic phase (22.9 g) is separated by column chromatography on silica gel. Elution with methylene chloride/toluene=13:7 gives 9.8 g of 1,2,6,7-tetramethyl-fluorenone ($R_f$ value 0.62) and 10.04 g of 2,3,6,7-tetramethyl-fluorenone ($R_f$ value 0.41). 2,3,6,7-Tetramethyl-fluorenone:

Melting point (toluene/ligroin): 254°–256° C.

| Elemental analysis: | | | |
|---|---|---|---|
| calculated | | found | |
| C | 86.41% | C | 86.3% |
| H | 6.83% | H | 6.7% |
| O | 6.77% | O | 6.8% |

1,2,6,7-Tetramethyl-fluorenone:
Melting point (toluene/ligroin): 263°–264° C.

| Elemental analysis: | | | |
|---|---|---|---|
| calculated | | found | |
| C | 86.41% | C | 86.5% |
| H | 6.83% | H | 7.1% |
| O | 6.77% | O | 6.9% |

Method B c) 3,4-Dimethyl-benzoic acid anhydride 88.6 ml of triethylamine are added dropwise to a mixture of 96.1 g of 3,4-dimethyl-benzoic acid and 108.1 g of dimethyl-benzoyl chloride in 600 ml of methylene chloride, while cooling with ice. After stirring at room temperature for 3.5 hours, the mixture is filtered. Evaporation of the filtrate and crystallisation of the residue from toluene gives 139 g of anhydride.

Melting point: 114–115° C.

Infrared spectrum (3% in chloroform): bands with maxima at 1,780 cm$^{-1}$ and 1,715 cm$^{-1}$.

(d) 2,3,6,7-Tetramethyl- and 1,2,6,7-tetramethyl-fluorenone

A mixture of 6.96 g of anhydride according to c) and 300 mg of tris-triphenylphosphine-rhodium(I) chloride is warmed in a heating bath of 240° C. in an argon atmosphere for 6 hours. After cooling, the mixture is taken up in chloroform and the resulting mixture is washed with 10% sodium hydroxide solution, dried (magnesium sulfate) and evaporated. Column chromatography of the residue according to b) gives 0.3 g of 1,2,6,7-tetramethyl-fluorenone and 0.94 g of 2,3,6,7-tetramethyl-fluorenone.

(e) Fluorenone-2,3,6,7-tetracarboxylic acid tetraethyl ester

A suspension of 0.7 g of tetramethyl-fluorenone in 60 ml of 20% nitric acid is warmed at 180° C. in a closed glass tube, with addition of a tantalum body, for 24 hours. The solution is evaporated, the residue is taken up in 25 ml of water and the mixture is filtered. The filtrate is evaporated, the residue (0.49 g) is dissolved in 40 ml of ethanol and, after addition of 0.1 ml of concentrated sulfuric acid, the mixture is refluxed for 24 hours. After addition of water, the mixture is extracted with chloroform. Column chromatography of the residue of the organic phase on silica gel with toluene/diethyl ether =20 : 1 as the eluting agent gives 143 mg of tetra-ester ($R_f$ value: 0.068).

Melting point (methylene chloride/hexane): 167°–168° C.

| Elemental analysis: | | | |
|---|---|---|---|
| calculated | | found | |
| C | 64.10% | C | 64.0% |
| H | 5.16% | H | 5.3% |
| O | 30.74% | O | 30.6% |

EXAMPLE 1

0.847 g (0.003 mole) of 4,4'-diamino-3,3'-dimethyl-5,5'-diethyldiphenylmethane is dissolved in 10 ml of N-methylpyrrolidone (NMP) in a cylindrical vessel with a stirrer, dropping funnel, internal thermometer, gas inlet tube and gas outlet tube, and the solution is cooled to 0° C., while simultaneously passing in nitrogen. A total of 1.018 g (0.00303 mole) of xanthonetetracarboxylic acid dianhydride is added in 4 portions (0.958 g, 0.03 g, 0.02 g, 0.01 g) to this solution in the course of 18 hours. Two hours after the last addition, 0.9 ml of triethylamine and 2.55 ml of acetic anhydride are added at room temperature and the mixture is stirred for 24 hours.

The polymer solution is then poured onto 1 litre of water and the polyimide is precipitated, filtered off and washed with water. Drying in vacuo at 80° C. gives 1.7 g of polyimide. The intrinsic viscosity, measured as a 0.5 percent solution in NMP, is 0.186 dl/g.

EXAMPLE 2

Example 1 is repeated, with the difference that 33.3 mol % of the diamine used therein is replaced by 3,6-diaminodurene.

EXAMPLE 3

Example 2 is repeated, with the difference that instead of the diamine used therein, a diamine of the formula

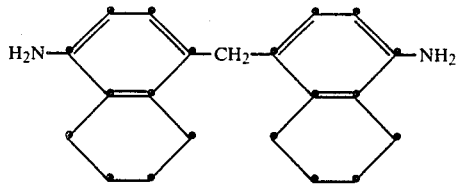

is employed. The intrinsic viscosity is 0.114 dl/g.

APPLICATION EXAMPLE

On a sheet of plastic laminated on one side with copper, a thin polymer film is produced by whirling on a 10 percent polymer solution in NMP and then removing the solvent in a circulating air oven.

The sheet thus coated is exposed through a photomask (Stouffer wedge) to light from a 1000 watt UV lamp from a distance of 18 cm at room temperature. The exposed sheet is then developed with NMP, the non-exposed areas of the polymer film being dissolved away. The relief image is subsequently rendered visible by etching away the copper coating thus exposed with FeCl$_3$ solution.

The photosensitivity is determined by the "21-step Stouffer sensitivity guide" and is, for the polymers from Examples 1, 2 and 3:

| Example | Exposure time | Last step imaged |
|---------|---------------|------------------|
| 1 | 120 sec | 6 |
| 2 | 240 sec | 8 |
| 3 | 420 sec | 4 |

EXAMPLE 4

Analogously to Example 1, a mixture of 2,4-di-amino-3,5-diethyltoluene and 4,4'-diamino-3,3',5,5'-tetramethyldiphenylmethane (1:1) is reacted with an equivalent amount of anthraquinone-2,3,6,7-tetracarboxylic acid dianhydride and the product is cyclised to the polyimide with triethylamine and acetic anhydride.

The intrinsic solution viscosity is 0.89 dl/g. The glass transition temperature, measured by differential scanning calorimetry (DSC), is 427° C. The photosensitivity according to the method in the application example is 5-6 steps at an exposure time of 30 seconds.

EXAMPLE 5

A diamine mixture as described in Example 2 is reacted analogously to Example 1 with the equivalent amount of 4,4'-ketodinaphthalic acid dianhydride and the product is cyclised to the polyimide.

The polyimide is likewise suitable for photographic production of relief images when irradiated with UV light.

EXAMPLE 6

1.64 g of 3,6-diaminodurene and 0.285 g of 3,4-dicarboxy-3'-aminobenzophenone are dissolved in 30 ml of N-methylpyrrolidone (NMP) in a flask with a stirrer and distillation attachment and the solution is heated to the boiling point. The water of reaction, together with about 10 ml of NMP, is distilled off in the course of about 30 minutes. 3.22 g of benzophenonetetracarboxylic acid dianhydride (BTDA) are added to the cooled solution and the solution is stirred for 5 hours. After addition of a further 32.2 mg of BTDA, the solution is stirred for another two hours. A mixture of 3 ml of triethylamine and 8.5 ml of acetic anhydride is then added to the solution. After stirring continuously for 16 hours, the polyimide is precipitated by pouring the solution into water and is filtered off, washed with water and dried.

Intrinsic viscosity: 0.52 dl/g

Glass transition temperature (DSC): 415° C.

The photosensitivity according to the application example is 7 steps at an exposure time of 60 seconds.

EXAMPLE 7

According to Example 1, a mixture of 0.651 g of 2,4-diamino-3,5-diethyltoluenediamine (0.0036 mole) and 2.400 g of 4,4'-diamino-3,3'-dimethyl-5,5'-diethyldiphenylmethane (0.0085 mole) in 29.5 ml of NMP is reacted with 4.278 g of thioxanthonetetracarboxylic acid dianhydride (0.0124 mole) to give the polyamide acid and, after addition of a further 20 ml of NMP, the product is then cyclised with acetic anhydride and triethylamine to give the polyimide.

Intrinsic solution viscosity: 0.79 dl/g

Glass transition temperature: 397° C.

The photosensitivity (according to the application example) is step 2 at an exposure time of 10 seconds.

What is claimed is:

1. A process for the preparation of a crosslinked protective coating on a carrier which comprises
    exposing to light or high-energy radiation a coating of a radiation-sensitive polymer applied on said carrier wherein the polymer is a homopolyimide or a copolyimide of at least one aromatic tetracarboxylic acid and at least one diamine, which essentially contains 0.1 to 100 mol % of at least one structural element of the formula I

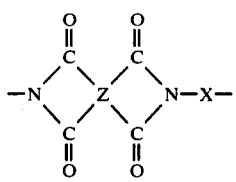  (I)

and 99.9 to 0 mol % of at least one structural element of the formulae II and/or III

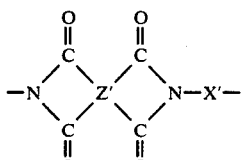  (II)

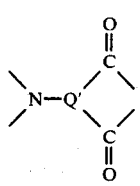  (III)

in which Z is at least one tetravalent radical of the formula IV, V, VI or VII

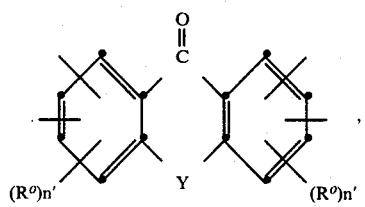  (IV)

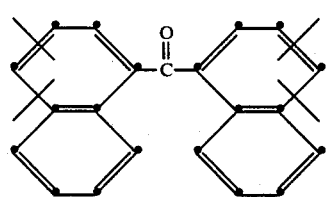  (V)

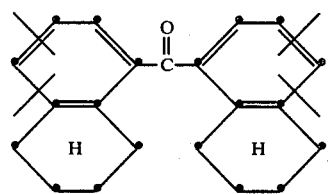  (VI)

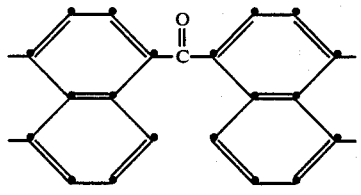  (VII)

in which the free bonds are in the ortho-position relative to one another and Y is direct bond, —CH$_2$—, —(CH$_2$)$_2$—, —O—, —S—, —SO—, —SO$_2$—, —CO—, —NR— or —CRR$^1$—, in which R is a hydrogen atom, C$_1$-C$_{10}$-alkyl, phenyl, naphthyl or phenyl-(C$_a$H$_{2a}$)-, where a is 1-4, and R$^1$ is R, with the exception of a hydrogen atom, Ro is C$_1$-C$_{10}$-alkyl, halogen, —CN, —NO$_2$, C$_1$-C$_{12}$-alkoxy, phenoxy, naphthoxy or phenyl-(C$_a$H$_{2a}$), where a is 1-4, n' is 0, 1 or 2, X is an unsubstituted or substituted divalent aliphatic radical, or said radical interrupted by heteroatoms or aromatic, heterocyclic or cyloaliphatic groups, a substituted or unsubstituted heterocyclic, cycloaliphatic or araliphatic radical, an aromatic radical, in which two aryl nuclei are linked via an aliphatic group, or an aromatic radical which is substituted by at least one alkyl group, cycloalkyl group, alkoxy group, alkoxyalkyl group, alkylthio group, alkylthioalkyl group, hydroxyalkyl group, hydroxyalkoxy group, hydroxyalkylthio group, aralkyl group or, in the case of two adjacent C atoms of the aromatic radical, by an alkylene group, Q' is a trivalent aromatic radical, Z' has the same meaning as Z or is a tetravalent organic radical othen than Z and X' is the divalent radical, other than X, of an organic diamine, and in which Z in formula I is also a tetravalent benzophenone radical if structural elements of the formula III are present.

2. A process according to claim 1 wherein the polymer is made from an acid of formula IV where Y is a direct bond, —CH$_2$—, —O—, —S— or —CO—.

3. A process according to claim 1 wherein the free bonds in the radicals of formula IV to VII are in the meta- or para-position relative to the CO group.

4. A process according to claim 1 where the substituent group on the aromatic radical x in the polymer contains 1 to 20 C atoms as alkyl or alkoxy, 2 to 12 C atoms as alkoxyalkyl, 5 or 6 ring carbon atoms as cycloakyl or 3 or 4 C atoms as alkylene, and is benzyl as aralkyl.

5. A process according to claim 4 wherein the substituent is alkyl with 1 to 4 C atoms.

6. A process according to claim 1 where in the polymer Z' is other than Z and contains 6 to 30 C atoms.

7. A process according to claim 6 wherein Z' is a radical of the formula

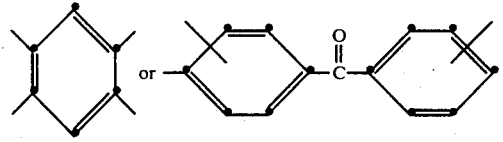

or a mixture thereof.

8. A process according to claim 1 where in the polymer one or two substituents on the aromatic radical X are bonded in the ortho-position relative to the N-atom.

9. A process according to claim 1 where in the structural element of formula I, X contains 2 to 30 C atoms as an aliphatic radical, 5 to 8 ring C atoms as a cycloaliphatic radical, 7 to 30 C atoms as an araliphatic radical or 7 to 30 C atoms as a substituted aromatic radical.

10. A process according to claim 1 where in the structural element of formula I, a substituted aromatic radical X has the formulae VIII, VIIIa and/or VIIIb

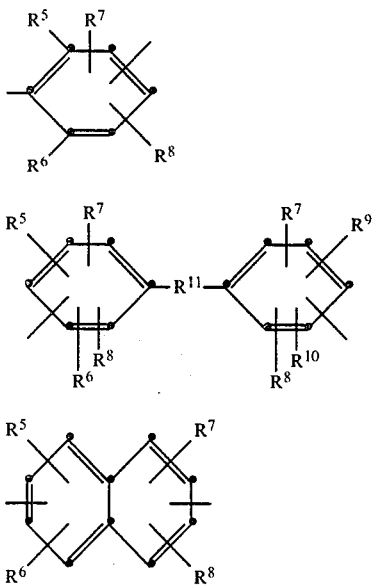 (VIII)

(VIIIa)

(VIIIb)

in which in formula VIII the free bonds are in the meta- or para-position relative to one another, in formula VIIIa the free bonds are in the meta-or para- position relative to the R¹¹ group and R⁵ and R⁶ are bonded in the two ortho-positions relative to the free bond, and in formula VIIIb the free bonds are in the 2-, 3-, 6- and 7-position and R⁵ and R⁶ are in the two ortho-positions relative to the free bonds, R¹¹ is a direct bond, —O—, —S—, —SS—, —SO—, —SO₂—, —CO—, —COO—, —NH—, -N-alkyl with 1 to 6 C atoms in the alkyl,

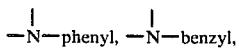

—CONH—, —CON-alkyl- with 1 to 6 C. atoms in the alkyl, -CON-phenyl-, -CON-benzyl-,

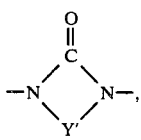

in which Y' is

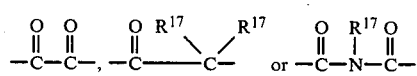

and R¹⁷ is a hydrogen atom, C₁-C₆-alkyl or phenyl, linear or branched alkylene with 1 to 3 C atoms, alkylidene with 2 to 12 C atoms which is unsubstituted or substituted by Cl or F, cycloalkylidene with 5 or 6 ring carbon atoms, phenylene, phenylenedioxy or the group

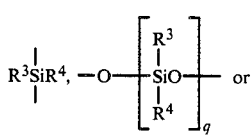

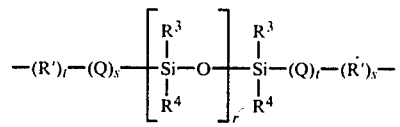

in which R³ and R⁴ are alkyl or alkoxy with 1 to 6 C atoms, phenyl, benzyl, phenoxy or benzyloxy, r is a number from 1 to 10, t is 0 or 1 and s is 0 or 1, and R' is —O— or —S— and Q is C₁-C₆-alkylene, and Q is a number from 1 to 100, R⁵ and R⁶ are alkyl, or alkoxy with 1 to 12 C atoms, alkoxyalkyl with 2 to 12 C atoms, cyclopentyl, cyclohexyl or benzyl, or in the formula VIII or VIIIa R⁵ and R⁷ are bonded in adjacent positions and together are trimethylene or tetramethylene, in which R⁶ is also a hydrogen atom, R⁷ and R⁸ are a hydrogen atom or independently have the meaning of R⁵ and R⁶, and R⁹ and R¹⁰ are a hydrogen atom, or independently have the meaning of R⁵ and R⁶, or R⁷ and R⁹ in formula VIIIa together are trimethylene or tetramethylene.

11. A process according to claim 10 wherein R⁵ and R⁶ are alkyl with 1 to 6 C. atoms.

12. A process according to claim 10 wherein R¹¹ is —CH₂—, —O—, —CO— or a direct bond.

13. A process according to claim 10 wherein the free bonds in formula VIIIa are in the para-position relative to the R¹¹ group.

14. A process according to claim 10 wherein X in formula I is a radical of the formula

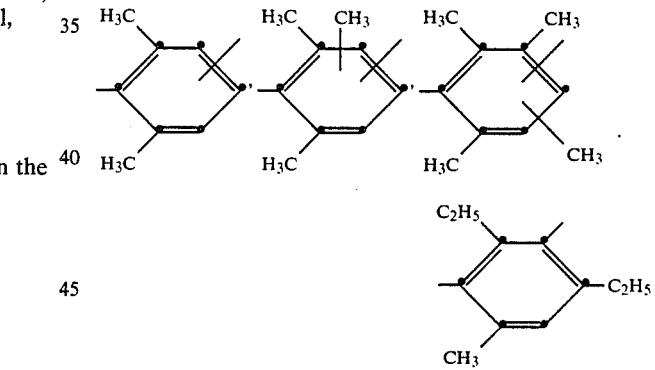

in which the free bonds are in the meta- or para-position relative to one another, or of the formula

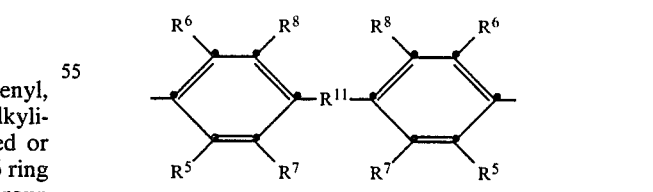

in which R⁵ and R⁶ independently are methyl, ethyl, n-propyl or isopropyl and R⁷ and R⁸ are a hydrogen atom or have the meaning of R⁵, or R⁵ and R⁷ together are trior tetramethylene and R⁶ and R⁸ are a hydrogen atom, and R¹¹ is a direct bond, CH₂ or CO.

15. A process according to claim 14 wherein the polymer is a copolyimide with two or more radicals of the formulae

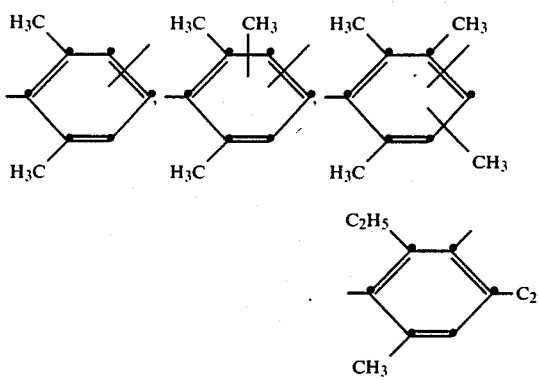

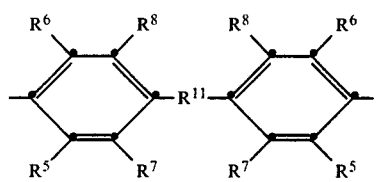

in which the free bonds are in the meta- or para-position relative to one another, and/or of the formula

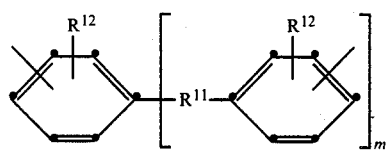

in which $R^5$, $R^6$, and $R^7$ and $R^8$ are methyl and $R^{11}$ is a direct bond, —$CH_2$— or —CO—.

16. A process according to claim 1 where in the polymer a substituted aromatic radical X has the formula IX

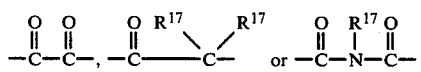 (IX)

in which m is 0 or 1, the free bonds are in the meta- or in the ortho-position relative to the $R^{12}$ group, $R^{11}$ is a direct bond, —O—, —S—, —SS—, —SO—, —$SO_2$—, —CO—, —COO—, —NH—, —N-alkyl with 1 to 6 C atoms in the alkyl, —N—phenyl, —N—benzyl, —CONH—, -CON-alkyl- with 1 to 6 C. atoms in the alkyl, -CON-phenyl-CON-benzyl-,

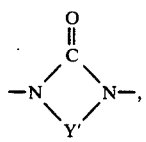

in which Y' is

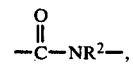

and $R^{17}$ is a hydrogen atom, $C_1$-$C_6$-alkyl or phenyl, linear or branched alkylene with 1 to 3 C atoms, alkylidene with 2 to 12 C atoms which is unsubstituted or substituted by Cl or F, cycloalkylidene with 5 or 6 ring carbon atoms, phenylene, phenylenedioxy or the group

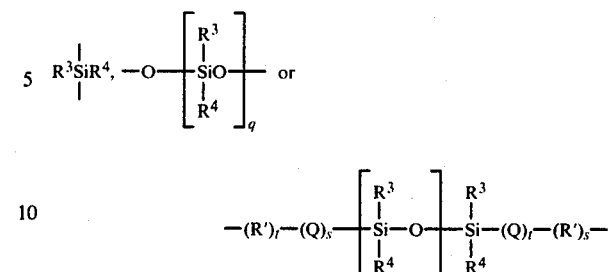

in which $R^3$ and $R^4$ are alkyl or alkoxy with 1 to 6 C atoms, phenyl, benzyl, phenoxy or benzyloxy, r is a number from 1 to 10, t is 0 or 1 and s is 0 or 1, and R' is —O— or -S- and Q is $C_1$-$C_6$-alkalene, an q is a number from 1 to 100, and $R^{12}$ is alkyl, or alkoxy with 1 to 12 C atoms, alkoxyalkyl with 2 to 12 C atoms, cyclopentyl, cyclohexyl or benzyl.

17. A process according to claim 1 where in the structural element of formula III, Q' is a trivalent radical of the formula

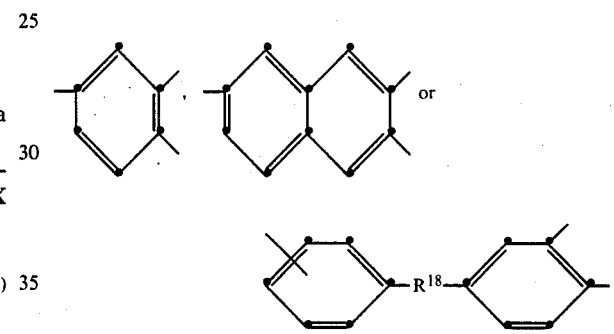

in which the free bond is in the meta- or para-position relative to the $R^{18}$ group and $R^{18}$ is a direct bond, —$CH_2$—, —O—, —S— or —CO—.

18. A process according to claim 1 where in the structural element of formula II, X' is phenylene which is unsubstituted or substituted by halogen or $C_1$-$C_4$-acyl, or bisphenylene of the formula

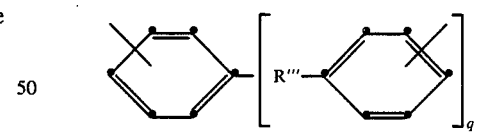

in which q is 0 or 1 and R''' is a direct bond, —O—, —S—, —SS—, —SO—, —$SO_2$—, —CO—, $$-\overset{O}{\underset{\|}{C}}-NR^2-,$$

—COO—, —$NR^2$—, —NH—, —CONH—, —$SiR^3$-$R^4$— or —$OSi(R^3R^4)O$—, and $R^2$, $R^3$ and $R^4$ are $C_1$-$C_6$-alkyl, phenyl or benzyl and $R^3$ and $R^4$ are also $C_1$-$C_6$-alkoxy, phenoxy or benzyloxy.

19. A process according to claim 1 where the polymer consists of structural elements of formula I, or of 2 to 4 structural elements of formulae I to III.

20. A process for the preparation of a relief image on a carrier which comprises exposing to light or high-energy radiation imagewise through a photomask a radiation-sensitive polymer applied on said carrier wherein the polymer is a homopolyimide or a copolyimide of at least one aromatic tetracarboxylic acid and at least one diamine, which essentially contains 0.1 to 100 ml % of at least one structural element of the formula I

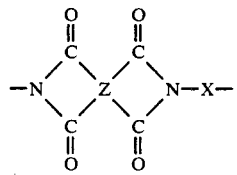

and 99.9 to 0 mol % of at least one structural element of the formulae II and/or III

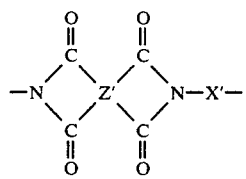

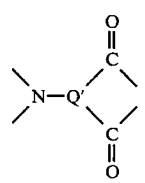

in which Z is at least one tetravalent radical of the formula IV, V, VI or VII

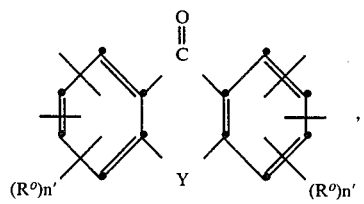

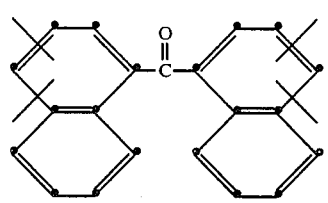

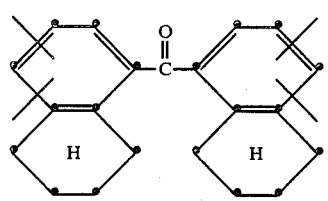

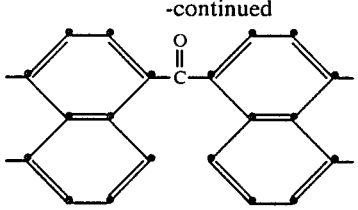

in which the free bonds are in the ortho-position relative to one another and Y is a direct bond, —$CH_2$—, —$(CH_2)_2$—, —O—, —S—, —SO—, —$SO_2$—, —CO—, —NR— or —$CRR^1$—, in which R is a hydrogen atom, $C_1$–$C_{10}$-alkyl, phenyl, naphthyl or phenyl($C_aH_{2a}$)-, where a is 1–4, and $R^1$ is R, with the exception of a hydrogen atom, $R^o$ is $C_1$–$C_{10}$-alkyl, halogen, —CN, —$NO_2$, $C_1$–$C_{12}$-alkoxy, phenoxy, naphthoxy or phenyl-($C_aH_{2a}$)-, where a is 1–4, n' is 0, 1 or 2, X is an unsubstituted or substituted divalent aliphatic radical, or said radical interrupted by heteroatoms or aromatic, heterocyclic or cycloaliphatic groups, a substituted or unsubstituted heterocyclic, cycloaliphatic or araliphatic radical, an aromatic radical, in which two aryl nuclei are linked via an aliphatic group, or an aromatic radical which is substituted by at least one alkyl group, cycloalkyl group, alkoxy group, alkoxyalkyl group, alkylthio group, alkylthioalkyl group, hydroxyalkyl group, hydroxyalkoxy group, hydroxyalkylthio group, aralkyl group or, in the case of two adjacent C atoms of the aromatic radical, by an alkylene group, Q' is a trivalent aromatic radical, Z' has the same meansing as Z or is a tetravalent organic radical other than Z and X' is the divalent radical, other than X, of an organic diamine, and in which Z in formula I is also a tetravalent benzophenone radical if structural elements of the formula III are present, and then removing the non-exposed portions with a solvent.

21. A process according to claim 20 wherein the polymer is made from an acid of formula IV where Y is a direct bond, —$CH_2$—, —O—, —S— or —CO—.

22. A process according to claim 20 wherein the free bonds in the radicals of formula IV to VII are in the meta- or para-position relative to the CO group.

23. A process according to claim 20 where the substituent group on the aromatic radical X in the polymer contains 1 to 20 C atoms as alkyl or alkoxy, 2 to 12 C atoms as alkoxyalkyl, 5 or 6 ring carbon atoms as cycloakyl or 3 or 4 C atoms as alkylene, and is benzyl as aralkyl.

24. A process according to claim 23 wherein the substituent is alkyl with 1 to 4 C atoms.

25. A process according to claim 23 where in the polymer Z' is other than Z and contains 6 to 30 C atoms.

26. A process according to claim 25 wherein Z' is a radical of the formula

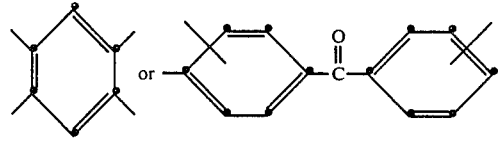

or a mixture thereof.

27. A process according to claim 20 where in the polymer one or two substituents on the aromatic radical X are bonded in the ortho-position relative to the N-atom.

28. A process according to claim 20 where in the structural element of formula I, X contains 2 to 30 C atoms as an aliphatic radical, 5 to 8 ring C atoms as a cycloaliphatic radical, 7 to 30 C atoms as an araliphatic radical or 7 to 30 C atoms as a substituted aromatic radical.

29. A process according to claim 20 where in the structural element of formula I, a substituted aromatic radical X has the formulae VIII, VIIIa and/or VIIIb

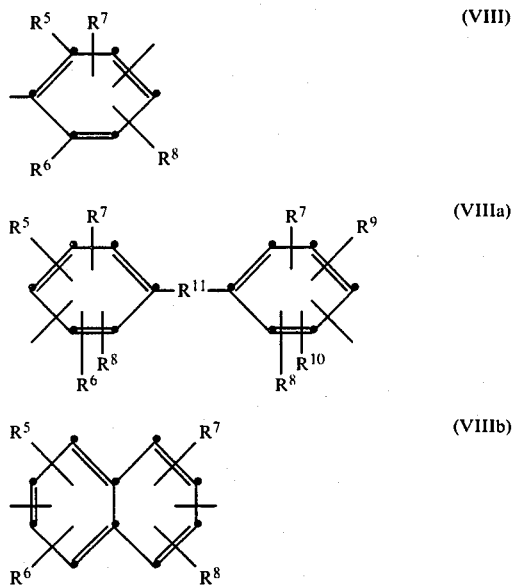

in which in formula VIII the free bonds are in the meta- or para-position relative to one another, in formula VIIIa the free bonds are in the meta- or para- position relative to the $R^{11}$ group and $R^5$ and $R^6$ are bonded in the two ortho-positions relative to the free bond, and in formula VIIIb the free bonds are in the 2-, 3,- 6- and 7-position and $R^5$ and $R^6$ are in the two ortho-positions relative to the free bonds, $R^{11}$ is a direct bond, —O—, —S—, —SS—, —SO—, —SO$_2$—, —CO—, —COO—, —NH—, —N-alkyl with 1 to 6 C atoms in the alkyl,

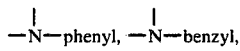

—CONH—, -CON-alkyl- with 1 to 6 C atoms in the alkyl, -CON-phenyl, -CON-benzyl,

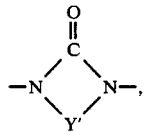

in which Y' is

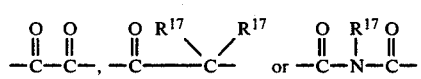

and $R^{17}$ is a hydrogen atom, $C_1$-$C_6$-alkyl or phenyl, linear or branched alkylene with 1 to 3 C atoms, alkylidene with 2 to 12 C atoms which is unsubstituted or substituted by Cl or F, cycloalkylidene with 5 or 6 ring carbon atoms, phenylene, phenylenedioxy or the group

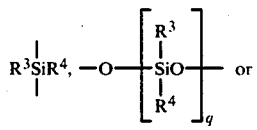

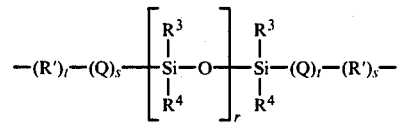

in which $R^3$ and $R^4$ are alkyl or alkoxy with 1 to 6 C atoms, plenyl, benzyl, phenoxy or benzyloxy, r is a number from 1 to 10, t is 0 or 1 and s is 0 or 1, and R' is —O— or —S— and Q is $C_1$-$C_6$-alkylene, and q is a number from 1 to 100, $R^5$ and $R^6$ are alkyl, or alkoxy with 1 to 12 C atoms, alkoxyalkyl with 2 to 12 C atoms, cyclopentyl, cyclohexyl or benzyl, or in the formula VIII or VIIa $R^5$ and $R^7$ are bonded in adjacent positions and together are trimethylene or tetramethylene, in which $R^6$ is also a hydrogen atom, $R^7$ and $R^8$ are a hydrogen atom or independently have the meaning of $R^5$ and $R^6$, and $R^9$ and $R^{10}$ are a hydrogen atom, or independently have the meaning of $R^5$ and $R^6$, or $R^7$ and $R^9$ in formula VIIIa together are trimethylene or tetramethylene.

30. A process according to claim 29 wherein $R^5$ and $R^6$ are alkyl with 1 to 6 C atoms.

31. A process according to claim 29 wherein $R^{11}$ is —CH$_2$—, —O—, —CO— or a direct bond.

32. A process according to claim 29 wherein the free bonds in formula VIIa are in the para-position relative to the $R^{11}$ group.

33. A process according to claim 29 wherein X in formula I is a radical of the formula

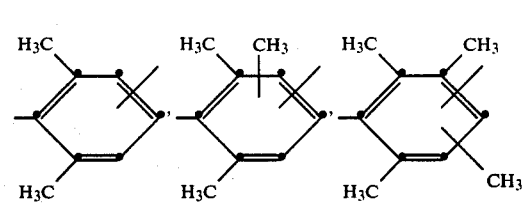

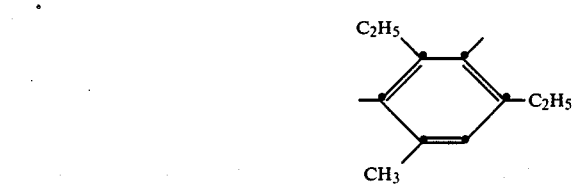

in which the free bonds are in the meta- or para-position relative to one another, or of the formula

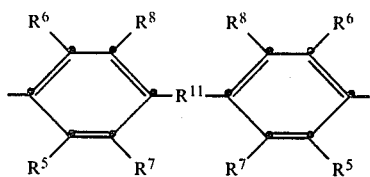

in which $R^5$ and $R^6$ independently are methyl, ethyl, n-propyl or isopropyl and $R^7$ and $R^8$ are a hydrogen atom or have the meaning of $R^5$, or $R^5$ and $R^7$ together are trior tetramethylene and $R^6$ and $R^8$ are a hydrogen atom, and $R^{11}$ is a direct bond, $CH_2$ or CO.

34. A process according to claim 33 wherein the polymer is a copolyimide with two or more radicals of the formulae

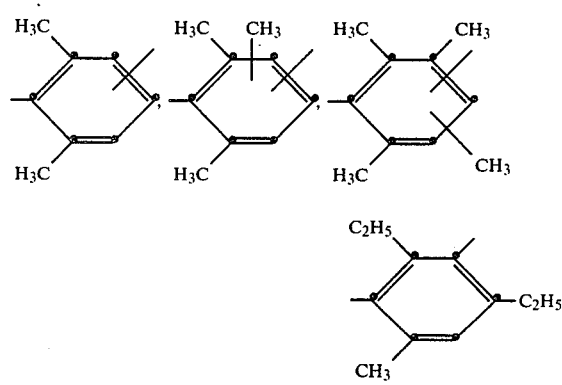

in which the free bonds are in the meta- or para-position relative to one another, and/or of the formula

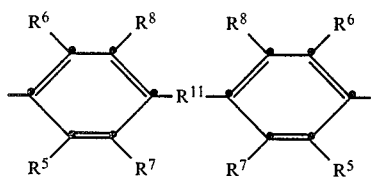

in which $R^5$, $R^6$, $R^7$ and $R^8$ are methyl and $R^{11}$ is a direct bond, $-CH_2-$ or $-CO-$.

35. A process according to claim 20 where in the polymer a substituted aromatic radical X has the formula IX

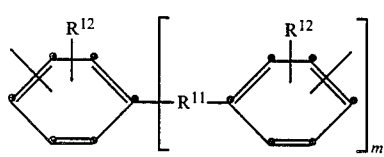

in which m is 0 or 1, the free bonds are in the meta- or in the ortho-position relative to the $R^{12}$ group, $R^{11}$ is a direct bond, $-O-$, $-S-$, $-SS-$, $-SO-$, $-SO_2-$, $-CO-$, $-COO-$, $-NH-$, -N-alkyl with 1 to 6 C atoms in the alkyl, $-N$-phenyl, $-N$-benzyl, -CONH-, -CON-alkyl- with 1 to 6 C atoms in the alkyl, -CON-phenyl- -CON-benzyl-,

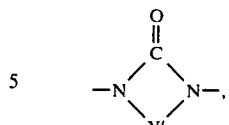

in which Y' is

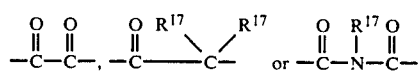

and $R^{17}$ is a hydrogen atom, $C_1-C_6$-alkyl or phenyl, linear or branched alkylene with 1 to 3 C atoms, alkylidene with 2 to 12 C atoms which is unsubstituted or substituted by Cl or F, cycloalkylidene with 5 or 6 ring carbon atoms, phenylene, phenylenedioxy or the group

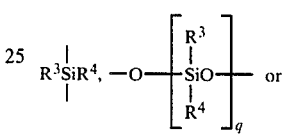

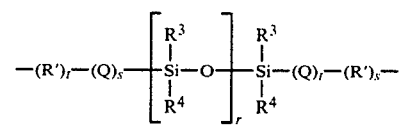

in which $R^3$ and $R^4$ are alkyl or alkoxy with 1 to 6 C atoms, phenyl, benzyl, phenoxy or benzyloxy, r is a number from 1 to 10, t is 0 or 1 and s is 0 or 1, and R' is $-O-$ or $-S-$ and Q is $C_1-C_6$-alkylene, and q is a number from 1 to 100, and $R^{12}$ is alkyl, or alkoxy with 1 to 12 C atoms, alkoxyalkyl with 2 to 12 C atoms, cyclopentyl, cyclohexyl or benzyl.

36. A process according to claim 20 where in the structural element of formula III, Q' is a trivalent radical of the formula

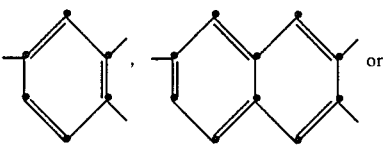

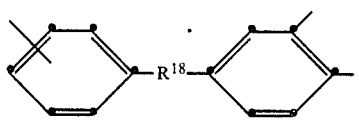

in which the free bond is in the meta- or para-position relative to the $R^{18}$ group and $R^{18}$ is a direct bond, $-CH_2-$, $-O-$, $-S-$ or $-CO-$.

37. A process according to claim 20 where in the structural element of formula II, X' is phenylene which is unsubstituted or substituted by halogen or $C_1-C_4$-acyl, or bisphenylene of the formula

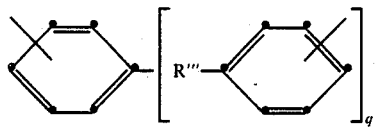
in which q is 0 or 1 and R''' is a direct bond, —O—, —S—, —SS—, —SO—, —SO$_2$—, —CO—,
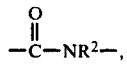
—COO—, —NR$^2$—, —NH—, —CONH—, —SiR$^3$R$^4$— or —OSi(R$^3$R$^4$)O—, and R$^2$, R$^3$ and R$^4$ are C$_1$–C$_6$-alkyl, phenyl or benzyl and R$^3$ and R$^4$ are also C$_1$–C$_6$-alkoxy, phenoxy or benzyloxy.
38. A process according to claim 20 where the polymer consists of stuctural elements of formula I, or of 2 to 4 structural elements of formulae I to III.
* * * * *